US009585721B2

(12) United States Patent
Daon

(10) Patent No.: US 9,585,721 B2
(45) Date of Patent: Mar. 7, 2017

(54) SYSTEM AND METHOD FOR REAL TIME TRACKING AND MODELING OF SURGICAL SITE

(71) Applicant: Navigate Surgical Technologies, Inc., Vancouver (CA)

(72) Inventor: Ehud (Udi) Daon, North Vancouver (CA)

(73) Assignee: Navigate Surgical Technologies, Inc., Vancouver, BC (CA)

( * ) Notice: Subject to any disclaimer, the term of this patent is extended or adjusted under 35 U.S.C. 154(b) by 253 days.

(21) Appl. No.: 14/645,927

(22) Filed: Mar. 12, 2015

(65) Prior Publication Data
US 2015/0182296 A1 Jul. 2, 2015

Related U.S. Application Data

(60) Continuation-in-part of application No. 14/599,149, filed on Jan. 16, 2015, now Pat. No. 9,452,024, which
(Continued)

(51) Int. Cl.
*A61B 5/055* (2006.01)
*A61B 19/00* (2006.01)
(Continued)

(52) U.S. Cl.
CPC ........ *A61B 19/5244* (2013.01); *A61B 5/0088* (2013.01); *A61B 5/064* (2013.01);
(Continued)

(58) Field of Classification Search
CPC ............ A61B 10/0233; A61B 17/3211; A61B 19/5244; A61B 2017/00477;
(Continued)

(56) References Cited

U.S. PATENT DOCUMENTS 5,230,623 A 7/1993 Guthrie
5,438,991 A 8/1995 Yu et al.
(Continued)

FOREIGN PATENT DOCUMENTS

DE 2005026654 12/2006
DE 2009009158 9/2010
(Continued)

OTHER PUBLICATIONS

Japanese Patent Office (JPO) Notice of Preliminary Rejection,Japan Patent Application No. 2014-537811, Based upon PCT/IL2012/000363, Jan. 25, 2016, which claims priority to U.S. Appl. No. 13/571,284, now U.S. Pat. No. 8,938,282.
(Continued)

*Primary Examiner* — Mark Remaly
(74) *Attorney, Agent, or Firm* — Kevin R. Erdman; Brannon Sowers & Cracraft PC

(57) ABSTRACT

The present invention involves a surgical site monitoring system and associated method of use employing vectorized 3D-tracking markers attached to a single vectorized fiducial reference and to a surgical site imaging sensor. A tracker obtains image information about both tracking markers and uses either the markings on or shapes of the tracking markers to determine from the image information the 3D locations and orientations of the imaging sensor and of the fiducial reference fixed to the surgical site. A scan taken of the surgical site prior to a surgical procedure with the fiducial reference attached allows live images of the surgery site to be sourced from the imaging sensor and to be overlaid in real time on a 3D model of the surgical site.

20 Claims, 14 Drawing Sheets

Related U.S. Application Data is a division of application No. 13/571,284, filed on Aug. 9, 2012, now Pat. No. 8,938,282, and a division of application No. 13/571,285, filed on Aug. 9, 2012, now Pat. No. 9,538,337.

(60) Provisional application No. 61/553,058, filed on Oct. 28, 2011, provisional application No. 61/952,832, filed on Mar. 13, 2014.

(51) Int. Cl.

| | | |
|---|---|---|
| *A61B 6/12* | (2006.01) | |
| *A61B 6/03* | (2006.01) | |
| *A61B 8/08* | (2006.01) | |
| *A61B 5/06* | (2006.01) | |
| *A61B 17/3211* | (2006.01) | |
| *A61C 1/08* | (2006.01) | |
| *A61B 5/00* | (2006.01) | |
| *A61B 6/14* | (2006.01) | |
| *A61B 10/02* | (2006.01) | |
| *A61C 1/00* | (2006.01) | |
| *A61B 17/00* | (2006.01) | |

(52) U.S. Cl.
CPC ........... *A61B 6/032* (2013.01); *A61B 6/12* (2013.01); *A61B 8/0841* (2013.01); *A61B 17/3211* (2013.01); *A61B 34/20* (2016.02); *A61B 90/16* (2016.02); *A61B 90/39* (2016.02); *A61C 1/082* (2013.01); *A61B 5/055* (2013.01); *A61B 6/14* (2013.01); *A61B 10/0233* (2013.01); *A61B 2017/00477* (2013.01); *A61B 2090/363* (2016.02); *A61B 2090/3925* (2016.02); *A61B 2090/3937* (2016.02); *A61B 2090/3954* (2016.02); *A61B 2090/3966* (2016.02); *A61B 2090/3983* (2016.02); *A61B 2090/3991* (2016.02); *A61C 1/0007* (2013.01)

(58) Field of Classification Search
CPC ...... A61B 2090/363; A61B 2090/3925; A61B 2090/3937; A61B 2090/3954; A61B 2090/3966; A61B 2090/3983; A61B 2090/3991; A61B 34/20; A61B 5/0088; A61B 5/055; A61B 5/064; A61B 6/032; A61B 6/12; A61B 6/14; A61B 8/0841; A61B 90/16; A61B 90/39; A61C 1/0007; A61C 1/082

See application file for complete search history.

(56) References Cited

U.S. PATENT DOCUMENTS

| | | | |
|---|---|---|---|
| 5,603,318 A | 2/1997 | Heilbrun et al. | |
| 5,828,770 A | 10/1998 | Leis et al. | |
| 5,967,777 A | 10/1999 | Klein | |
| 6,122,541 A | 9/2000 | Cosman et al. | |
| 6,468,265 B1 | 10/2002 | Evans et al. | |
| 6,529,765 B1 | 3/2003 | Franck et al. | |
| 7,653,455 B2 | 1/2010 | Cinador | |
| 7,720,521 B2 | 5/2010 | Chang | |
| 7,758,345 B1 | 7/2010 | Christensen | |
| 7,894,878 B2 | 2/2011 | Noujeim | |
| 7,899,512 B2 | 3/2011 | Labadie | |
| 8,014,575 B2 | 9/2011 | Weiss et al. | |
| 8,172,573 B2 | 5/2012 | Sonenfeld | |
| 2004/0002642 A1 | 1/2004 | Dekel et al. | |
| 2004/0097952 A1 | 5/2004 | Sarin et al. | |
| 2004/0138556 A1 | 7/2004 | Cosman | |
| 2004/0152970 A1 | 8/2004 | Hunter | |
| 2005/0085719 A1 | 4/2005 | Franklin et al. | |
| 2005/0163342 A1 | 7/2005 | Persky | |
| 2005/0182318 A1 | 8/2005 | Kaji et al. |
| 2005/0182320 A1 | 8/2005 | Stifter |
| 2006/0142657 A1 | 6/2006 | Quaid et al. |
| 2006/0165310 A1 | 7/2006 | Mack |
| 2006/0212044 A1 | 9/2006 | Bova et al. |
| 2006/0247517 A1 | 11/2006 | Labadie et al. |
| 2006/0281991 A1 | 12/2006 | Fitzpatrick |
| 2007/0208252 A1 | 9/2007 | Makower |
| 2007/0223910 A1 | 9/2007 | Aoki |
| 2007/0253541 A1 | 11/2007 | Sukovic et al. |
| 2008/0026338 A1 | 1/2008 | Cinader |
| 2008/0135733 A1 | 6/2008 | Feilkas et al. |
| 2008/0161682 A1 | 7/2008 | Kendrick et al. |
| 2008/0171305 A1 | 7/2008 | Sonenfeld et al. |
| 2008/0183071 A1 | 7/2008 | Strommer |
| 2008/0193896 A1 | 8/2008 | Yang |
| 2008/0200927 A1 | 8/2008 | Hartmann et al. |
| 2008/0262345 A1 | 10/2008 | Fichtinger |
| 2008/0319491 A1 | 12/2008 | Schoenefeld |
| 2009/0012509 A1 | 1/2009 | Csavoy |
| 2009/0171196 A1 | 7/2009 | Olson et al. |
| 2009/0253095 A1 | 10/2009 | Salcedo |
| 2010/0039506 A1 | 2/2010 | Sarvestani et al. |
| 2010/0049195 A1 | 2/2010 | Park et al. |
| 2010/0168562 A1 | 7/2010 | Zhao et al. |
| 2010/0168763 A1 | 7/2010 | Zhao et al. |
| 2010/0210939 A1 | 8/2010 | Hartmann et al. |
| 2010/0217139 A1 | 8/2010 | Pinter et al. |
| 2011/0008751 A1 | 1/2011 | Patterssen |
| 2011/0087332 A1 | 4/2011 | Bojarski et al. |
| 2011/0217667 A1 | 9/2011 | Groscruth |
| 2011/0257653 A1 | 10/2011 | Hughes |
| 2012/0065496 A1 | 3/2012 | Stratton |
| 2012/0115107 A1 | 5/2012 | Adams |
| 2012/0253186 A1 | 10/2012 | Simpson et al. |
| 2012/0259204 A1 | 10/2012 | Carrat et al. |
| 2012/0283637 A1 | 11/2012 | Cohen |
| 2013/0063558 A1 | 3/2013 | Phipps |
| 2013/0122463 A1 | 5/2013 | Csillag |
| 2013/0218024 A1 | 8/2013 | Boctor |
| 2013/0258353 A1 | 10/2013 | Kosmecki et al. |
| 2013/0332271 A1 | 12/2013 | Hay |
| 2014/0030669 A1 | 1/2014 | Hey et al. |
| 2014/0049629 A1 | 2/2014 | Siewerdsen et al. |
| 2014/0199650 A1 | 7/2014 | Moffson |
| 2015/0178992 A1 | 6/2015 | Bhuruth |

FOREIGN PATENT DOCUMENTS

| | | |
|---|---|---|
| DE | 2010042540 | 4/2012 |
| DE | 2011012460.8 | 8/2012 |
| EP | 1442715 A2 | 8/2004 |
| EP | 1527417 | 9/2011 |
| FR | 2 929 794 | 10/2009 |
| GB | 2 416 949 | 2/2006 |
| JP | 2000046546 | 2/2000 |
| JP | 2007253748 | 10/2007 |
| JP | 2009172411 | 5/2009 |
| WO | 99/27839 | 6/1999 |
| WO | 02/076302 | 10/2002 |
| WO | 03096920 A1 | 11/2003 |
| WO | 2008/009136 | 1/2008 |
| WO | 2010/086374 | 5/2010 |
| WO | 2011012460 A2 | 2/2011 |
| WO | 2011113441 | 9/2011 |
| WO | 2013144939 | 4/2012 |
| WO | 2012068679 | 5/2012 |
| WO | 2012095642 | 7/2012 |
| WO | 2012149548 | 11/2012 |
| WO | 2012149548 A2 | 11/2012 |
| WO | 2013010138 A2 | 1/2013 |
| WO | 2013055707 A1 | 4/2013 |
| WO | 2013096766 | 6/2013 |
| WO | 2011/109041 | 10/2013 |
| WO | 2013144208 | 10/2013 |
| WO | 2014147601 A2 | 9/2014 |
| WO | 2014201968 A1 | 12/2014 |

(56) References Cited

FOREIGN PATENT DOCUMENTS

OTHER PUBLICATIONS

Japanese Patent Office (JPO) Notice of Preliminary Rejection,Japanese Patent Application No. 2015-541159, Based upon PCT/EP2013/0073401, Mar. 1, 2016, which claims priority to U.S. Appl. No. 14/562,691, now U.S. Pat. No. 8,908,918 0.
European Patent Office, Written Opinion of the International Searching Authority, International Application No. PCT/IL2015/050400, Navigate Surgical Technologies, Inc., Jul. 16, 2015.
European Patent Office, International Search Report, International Application No. PCT/IL2015/050400, Navigate Surgical Technologies, Inc., Jul. 16, 2015.
USPTO, Non-Final Office Action for U.S. Appl. No. 13/744,967, dated Jun. 30, 2015.
USPTO, Non-Final Office Action for U.S. Appl. No. 13/745,249, dated Jun. 30, 2015.
USPTO, Final Office Action for U.S. Appl. No. 13/745,763, dated Jul. 8, 2015.
Arizona Center for Laser Dentistry, Root Canals at the Arizona Center for Laser Dentistry, Captured via web.archive.org on Dec. 19, 2010, retrieved Jun. 2, 2015.
European Patent Office, International Search Report for PCT/EP2016/054110, Jun. 10, 2016.
European Patent Office, International Written Opinion, dated Sep. 29, 2014 (PCT/IB2014/060403).
European Patent Office, International Written Opinion, dated Oct. 17, 2014 (PCT/EP2014/067280).
European Patent Office, International Search Report, dated Jul. 17, 2014 (PCT/EP2014/058406).
European Patent Office, International Written Opinion, dated Aug. 18, 2014 (PCT/EP2014/058406).
European Patent Office, International Written Opinion, dated Jul. 30, 2014 (PCT/EP2014/057656).
European Patent Office, International Written Opinion, dated Jul. 30, 2014 (PCT/EP2014/060018).
EPO, International Search Report and Written Opinion for PCT/Ep/2013/073401, Mar. 7, 2014.
European Patent Office, International Search Report, dated Sep. 3, 2013 (PCT/IL2013/000032).
European Patent Office, International Written Opinion, dated Sep. 3, 2013 (PCT/IL2013/000032).
European Patent Office, International Search Report, dated Sep. 16, 2013 (PCT/EP2013/056525).
European Patent Office, International Written Opinion, dated Sep. 16, 2013 (PCT/EP2013/056525).
European Patent Office, International Search Report, mailed Sep. 17, 2013 (PCT/IL2013/000031).
European Patent Office, International Written Opinion, mailed Sep. 17, 2013 (PCT/IL2013/000031).
Prosecution of U.S. Appl. No. 13/571,284, from First Office Action of Aug. 15, 2013 to Amendment with Request for Continued Examination of Feb. 26, 2014.
European Patent Office, International Search Report, mailed Mar. 4, 2013 (PCT/IL2012/000363).
European Patent Office, International Written Opinion, mailed Mar. 4, 2013 (PCT/IL2012/000363).
European Patent Office, International Search Report, dated Feb. 18, 2014 (PCT/EP2013/073416).
European Patent Office, International Written Opinion, dated Feb. 18, 2014 (PCT/EP2013/073416).
European Patent Office, International Search Report, International Application No. PCT/EP2013/073401, dated Mar. 19, 2014.
European Patent Office, Written Opinion of the International Searching Authority, International Application No. PCT/EP2013/073401, dated Mar. 19, 2014.
European Patent Office, International Search Report, International Application No. PCT/EP2014/057656, dated Aug. 11, 2014.
European Patent Office, Written Opinion of the International Searching Authority, International Application No. PCT/EP2014/051656, dated Aug. 11, 2014.
European Patent Office, International Search Report, International Application No. PCT/EP2014/060018, dated Aug. 11, 2014.
European Patent Office, Written Opinion of the International Searching Authority, International Application No. PCT/EP2014/060018, dated Aug. 11, 2014.
European Patent Office, Written Opinion of the International Searching Authority, International Application No. PCT/EP2014/067279, dated Nov. 7, 2014.
European Patent Office, Written Opinion of the International Searching Authority, International Application No. PCT/EP2014/067280, dated Oct. 27, 2014.
USPTO, Non-Final Office Action for U.S. Appl. No. 13/571,284, dated Aug. 15, 2013.
USPTO, Non- Final Office Action for U.S. Appl. No. 13/713,165, dated Aug. 13, 2014.

SYSTEM AND METHOD FOR REAL TIME TRACKING AND MODELING OF SURGICAL SITE

CROSS REFERENCE TO RELATED APPLICATIONS

The present application claims priority under 35 U.S.C. §119(e) of U.S. Provisional Patent Application Ser. No. 61/952,832, filed Mar. 13, 2014; and is a continuation-in-part of U.S. patent application Ser. No. 14/599,149, filed Jan. 16, 2015, which is a divisional application of U.S. patent application Ser. No. 13/571,284, filed Oct. 28, 2011, and also claims priority to Ser. No. 13/822,358, filed Mar. 12, 2013, both of which claim priority under 35 U.S.C. §119(e) of U.S. Provisional Patent Application Ser. No. 61/553,056, filed Oct. 28, 2011, and 61/616,718, filed Mar. 28, 2012, the disclosures of which are incorporated by reference herein.

BACKGROUND OF THE INVENTION

Field of the Invention

The invention relates to location monitoring hardware and software systems. More specifically, the field of the invention is that of surgical equipment and software for monitoring surgical conditions.

Description of the Related Art

Visual and other sensory systems are known, with such systems being capable of both observing and monitoring surgical procedures. With such observation and monitoring systems, computer aided surgeries are now possible, and in fact are being routinely performed. In such procedures, the computer software interacts with both clinical images of the patient and observed surgical images from the current surgical procedure to provide guidance to the physician in conducting the surgery. For example, in one known system a carrier assembly bears at least one fiducial marker onto an attachment element in a precisely repeatable position with respect to a patient's jaw bone, employing the carrier assembly for providing registration between the fiducial marker and the patient's jaw bone and implanting the tooth implant by employing a tracking system which uses the registration to guide a drilling assembly. With this relatively new computer implemented technology, further improvements may further advance the effectiveness of surgical procedures.

SUMMARY OF THE INVENTION

The present invention involves embodiments of surgical hardware and software monitoring system and method which allows for surgical planning while the patient is available for surgery, for example while the patient is being prepared for surgery so that the system may model the surgical site. In one embodiment, the model may be used to track contemplated surgical procedures and warn the physician regarding possible boundary violations that would indicate an inappropriate location in a surgical procedure. In another embodiment, the hardware may track the movement of instruments during the procedure and in reference to the model to enhance observation of the procedure. In this way, physicians are provided an additional tool to improve surgical planning and performance.

The system uses a single particularly configured vectorized fiducial reference, to orient the monitoring system with regard to the critical area. The fiducial reference is attached to a location near the intended surgical area. For example, in the example of a dental surgery, a splint may be used to securely locate the fiducial reference near the surgical area. The fiducial reference may then be used as a point of reference, or a fiducial, for the further image processing of the surgical site. The fiducial reference may be identified relative to other portions of the surgical area by having a recognizable fiducial marker apparent in the scan.

The embodiments of the invention involve automatically computing the three-dimensional location of the patient by means of a tracking marker. The tracking marker is vectorized and may be attached in fixed spatial relation either directly to the fiducial reference, or attached to the fiducial reference via a tracking pole that itself may have a distinct three-dimensional shape. In the dental surgery example, a tracking pole is mechanically connected to the base of the fiducial reference that is in turn fixed in the patient's mouth. Each tracking pole device has a particular observation pattern, located either on itself or on a suitable tracking marker, and a particular geometrical connection to the base, which the computer software recognizes as corresponding to a particular geometry for subsequent location calculations. Although individual tracking pole devices have distinct configurations, they may all share the same connection base and thus may be used with any fiducial reference. The particular tracking information calculations are dictated by the particular tracking pole used, and actual patient location is calculated accordingly. Thus, tracking pole devices may be interchanged and calculation of the location remains the same. This provides, in the case of dental surgery, automatic recognition of the patient head location in space. Alternatively, a sensor device, or a tracker, may be in a known position relative to the fiducial key and its tracking pole, so that the current data image may be mapped to the scan image items.

The fiducial reference and each tracking pole or associated vectorized tracking marker may have a pattern made of radio opaque material so that when imaging information is scanned by the software, the particular items are recognized. Typically, each instrument used in the procedure has a unique pattern on its associated tracking marker so that the tracker information identifies the instrument. The software creates a model of the surgical site, in one embodiment a coordinate system, according to the location and orientation of the patterns on the fiducial reference and/or tracking pole(s) or their attached tracking markers. By way of example, in the embodiment where the fiducial reference has an associated pre-assigned pattern, analysis software interpreting image information from the tracker may recognize the pattern and may select the site of the base of the fiducial to be at the location where the fiducial reference is attached to a splint. If the fiducial key does not have an associated pattern, a fiducial site is designated. In the dental example this can be at a particular spatial relation to the tooth, and a splint location can be automatically designed for placement of the fiducial reference.

An in situ imager, tagged with a suitable vectorized tracking marker, provides live imagery of the surgical site. The tracking marker on the imager is tracked by the tracker of the system. Since the mutual relative locations and orientations of the in situ imager and the tracking marker are known, the controller of the system may derive the location and orientation of the imager by tracking the marker on the imager. This allows the exact view of the imager to be computed and live imagery from the in situ imager to be overlaid on a model of the surgical site in real time.

In a first aspect, a position monitoring system is presented for a surgical procedure comprising: a single vectorized fiducial reference adapted to be fixed to a surgical site of a surgical patient; an imaging sensor adapted for disposing proximate the surgical site and adapted for obtaining live images of the surgical site; an illuminator adapted for illuminating the surgical site with radiation; a first vectorized tracking marker rigidly attached in a predetermined fixed three-dimensional position and orientation relative to the single fiducial reference; a second vectorized tracking marker rigidly attached in a predetermined fixed three-dimensional position and orientation relative to the imaging sensor; a tracker configured and disposed for obtaining image information of at least the first and second tracking markers; scan data of the surgical site before the surgical procedure with the single fiducial reference fixed to the surgical site; a controller data-wise coupled to the tracker and to the imaging sensor and comprising a processor with memory and a software program having a series of instructions which when executed by the processor determines from the image information current positions and orientations of the first and second tracking markers, and relates the scan data to the current three-dimensional position and orientation of the single fiducial reference and to the current live image of the surgical site; and a display system data-wise coupled to the controller and adapted to show during the surgical procedure the current live image of the surgical site in three-dimensional spatial relationship relative to the scan data. The tracker may be an optical tracker. More specifically, the tracker may be a non-stereo optical tracker. In other embodiments, the tracker may be a stereo optical tracker. The single fiducial reference may be at least partially non-visible when fixed to the surgical site.

The system may further comprise a surgical implement bearing a third vectorized tracking marker, wherein the tracker is further configured and disposed for obtaining image information of the third tracking marker; the software program has a further series of instructions which when executed by the processor determines from the image information the current position and orientation of the third tracking marker and relates the scan data to the current position and orientation of the surgical implement.

In another aspect, a method is presented for monitoring a surgical site, comprising: removably attaching a single vectorized fiducial reference to a fiducial location proximate a surgical site, the fiducial reference having at least one of a marking and a shape perceptible on a scan; creating prior to the surgical procedure a scan of the surgical site and the fiducial location with the single fiducial reference attached; removably and rigidly attaching to the single fiducial reference a first vectorized tracking marker disposed within a field of view of a tracker; disposing proximate the surgical site an imaging sensor bearing a second vectorized tracking marker disposed in the field of view of tracker; receiving from the tracker image information of at least the surgical site and the first and second tracking markers; obtaining from the imaging sensor live images of the surgical site; determining from the scan data, the image information, and the live images of the surgical site a continuously updated 3-dimensional model of the surgical site overlaid with live imagery of the surgical site. The removably attaching the single fiducial reference may be removably attaching the single fiducial reference to be disposed at least partly non-visible to the tracker. The receiving image information may be receiving optical image information. In particular, the receiving optical image information may be receiving non-stereo optical image information. The obtaining live images may comprise one of obtaining live optical images and obtaining live X-ray transmission images. The obtaining live optical images may comprise be one or both of obtaining live optical images based on reflected light and obtaining live fluoroscopic images. The obtaining live images may comprise illuminating the surgical site with at least one of X-ray radiation, exciting radiation, and reflective optical radiation by means of the illuminator.

The determining the continuously updated three-dimensional model of the surgical site may comprise: determining from the first scan data a three-dimensional location and orientation of the single vectorized fiducial reference relative to the surgical site based on at least one of markings on and the shape of the single fiducial reference; determining from the image information three-dimensional location and orientation information about the first and second vectorized tracking markers; and calculating from the three-dimensional locations and orientations of the first and second tracking markers the corresponding three-dimensional locations and orientations of the single fiducial reference and imaging sensor, respectively.

The determining the continuously updated three-dimensional model of the surgical site may further comprise: determining from the image information three-dimensional location and orientation information about a third vectorized tracking marker fixedly attached to a surgical implement; and calculating from the three-dimensional location and orientation of the third tracking marker the corresponding three-dimensional location and orientation of the surgical implement.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Figure 1:
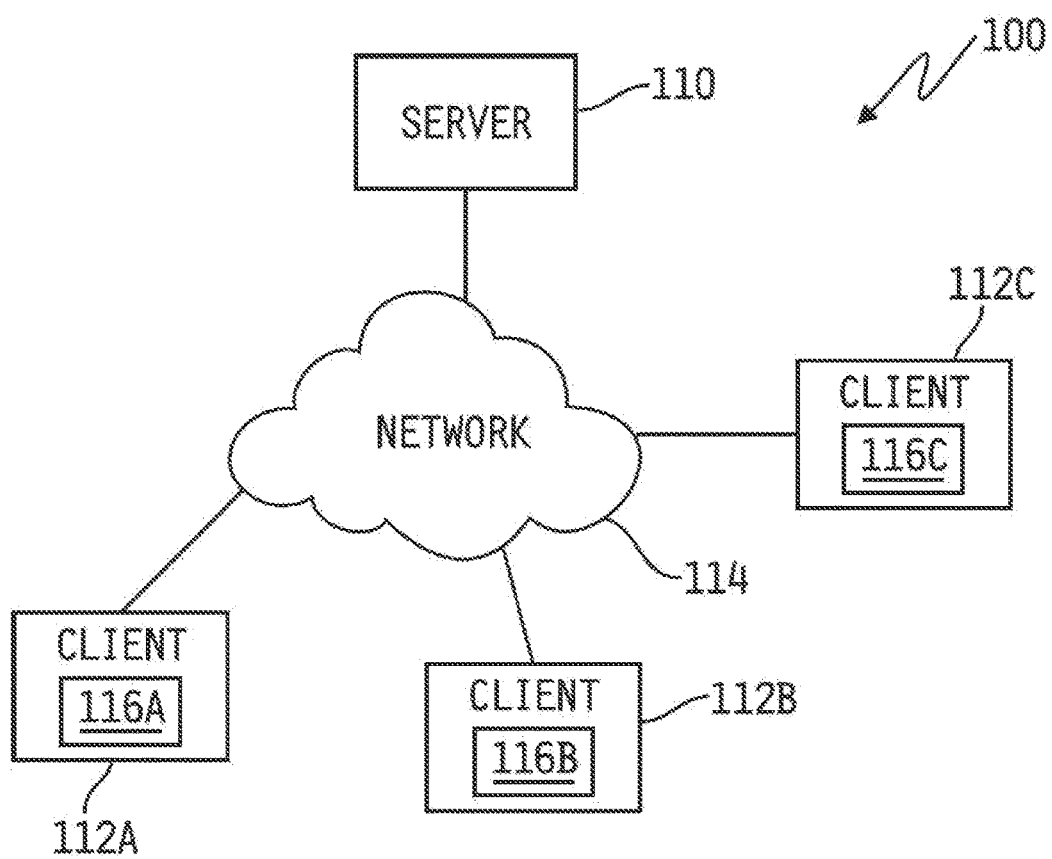
FIG. 1 is a schematic diagrammatic view of a network system in which embodiments of the present invention may be utilized.

Corresponding reference characters indicate corresponding parts throughout the several views. Although the drawings represent embodiments of the present invention, the drawings are not necessarily to scale and certain features may be exaggerated in order to better illustrate and explain the present invention. The flow charts and screen shots are also representative in nature, and actual embodiments of the invention may include further features or steps not shown in the drawings. The exemplification set out herein illustrates an embodiment of the invention, in one form, and such exemplifications are not to be construed as limiting the scope of the invention in any manner.

DESCRIPTION OF EMBODIMENTS OF THE PRESENT INVENTION

The embodiments disclosed below are not intended to be exhaustive or limit the invention to the precise form disclosed in the following detailed description. Rather, the embodiments are chosen and described so that others skilled in the art may utilize their teachings.

The detailed descriptions that follow are presented in part in terms of algorithms and symbolic representations of operations on data bits within a computer memory representing alphanumeric characters or other information. The hardware components are shown with particular shapes and relative orientations and sizes using particular scanning techniques, although in the general case one of ordinary skill recognizes that a variety of particular shapes and orientations and scanning methodologies may be used within the teaching of the present invention. A computer generally includes a processor for executing instructions and memory for storing instructions and data, including interfaces to obtain and process imaging data. When a general-purpose computer has a series of machine encoded instructions stored in its memory, the computer operating on such encoded instructions may become a specific type of machine, namely a computer particularly configured to perform the operations embodied by the series of instructions. Some of the instructions may be adapted to produce signals that control operation of other machines and thus may operate through those control signals to transform materials far removed from the computer itself. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities, observing and measuring scanned data representative of matter around the surgical site. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as bits, values, symbols, characters, display data, terms, numbers, or the like as a reference to the physical items or manifestations in which such signals are embodied or expressed to capture the underlying data of an image. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements that impart or manifest a physical organization on the information stored in memory. More than mere abstraction, the data structures are specific electrical or magnetic structural elements in memory, which simultaneously represent complex data accurately, often data modeling physical characteristics of related items, and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein that form part of the present invention; the operations are machine operations. Useful machines for performing the operations of the present invention include general-purpose digital computers or other similar devices. In all cases the distinction between the method operations in operating a computer and the method of computation itself should be recognized. The present invention relates to a method and apparatus for operating a computer in processing electrical or other (e.g., mechanical, chemical) physical signals to generate other desired physical manifestations or signals. The computer operates on software modules, which are collections of signals stored on a media that represents a series of machine instructions that enable the computer processor to perform the machine instructions that implement the algorithmic steps. Such machine instructions may be the actual computer code the processor interprets to implement the instructions, or alternatively may be a higher level coding of the instructions that is interpreted to obtain the actual computer code. The software module may also include a hardware component, wherein some aspects of the algorithm are performed by the circuitry itself rather as a result of an instruction.

The present invention also relates to an apparatus for performing these operations. This apparatus may be specifically constructed for the required purposes or it may comprise a general-purpose computer as selectively activated or reconfigured by a computer program stored in the computer. The algorithms presented herein are not inherently related to any particular computer or other apparatus unless explicitly indicated as requiring particular hardware. In some cases, the computer programs may communicate or relate to other programs or equipments through signals configured to particular protocols, which may or may not require specific hardware or programming to interact. In particular, various general-purpose machines may be used with programs written in accordance with the teachings herein, or it may prove more convenient to construct more specialized apparatus to perform the required method steps. The required structure for a variety of these machines will appear from the description below.

The present invention may deal with "object-oriented" software, and particularly with an "object-oriented" operating system. The "object-oriented" software is organized into "objects", each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects. Often, but not necessarily, a physical object has a corresponding software object that may collect and transmit observed data from the physical device to the software system. Such observed data may be accessed from the physical object and/or the software object merely as an item of convenience; therefore where "actual data" is used in the following description, such "actual data" may be from the instrument itself or from the corresponding software object or module.

Messages are sent and received between objects having certain functions and knowledge to carry out processes. Messages are generated in response to user instructions, for example, by a user activating an icon with a "mouse" pointer generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and here the other objects are not allowed to access. One feature of the object-oriented system is inheritance. For example, an object for drawing a "circle" on a display may inherit functions and knowledge from another object for drawing a "shape" on a display.

A programmer "programs" in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of the system may be modeled with an object, the behavior of each component being simulated by the methods of its corresponding object, and the interactions between components being simulated by messages transmitted between objects.

An operator may stimulate a collection of interrelated objects comprising an object-oriented program by sending a message to one of the objects. The receipt of the message may cause the object to respond by carrying out predetermined functions, which may include sending additional messages to one or more other objects. The other objects may in turn carry out additional functions in response to the messages they receive. Including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

Although object-oriented programming makes simulation of systems of interrelated components more intuitive, the operation of an object-oriented program is often difficult to understand because the sequence of operations carried out by an object-oriented program is usually not immediately apparent from a software listing as in the case for sequentially organized programs. Nor is it easy to determine how an object-oriented program works through observation of the readily apparent manifestations of its operation. Most of the operations carried out by a computer in response to a program are "invisible" to an observer since only a relatively few steps in a program typically produce an observable computer output.

In the following description, several terms that are used frequently have specialized meanings in the present context. The term "object" relates to a set of computer instructions and associated data, which may be activated directly or indirectly by the user. The terms "windowing environment", "running in windows", and "object oriented operating system" are used to denote a computer user interface in which information is manipulated and displayed on a video display such as within bounded regions on a raster scanned video display. The terms "network", "local area network", "LAN", "wide area network", or "WAN" mean two or more computers that are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks may access the network resources, such as shared data files, common peripheral devices, and inter-workstation communication. Users activate computer programs or network resources to create "processes" which include both the general operation of the computer program along with specific operating characteristics determined by input variables and its environment. Similar to a process is an agent (sometimes called an intelligent agent), which is a process that gathers information or performs some other service without user intervention and on some regular schedule. Typically, an agent, using parameters typically provided by the user, searches locations either on the host machine or at some other point on a network, gathers the information relevant to the purpose of the agent, and presents it to the user on a periodic basis.

The term "desktop" means a specific user interface which presents a menu or display of objects with associated settings for the user associated with the desktop. When the desktop accesses a network resource, which typically requires an application program to execute on the remote server, the desktop calls an Application Program Interface, or "API", to allow the user to provide commands to the network resource and observe any output. The term "Browser" refers to a program which is not necessarily apparent to the user, but which is responsible for transmitting messages between the desktop and the network server and for displaying and interacting with the network user. Browsers are designed to utilize a communications protocol for transmission of text and graphic information over a worldwide network of computers, namely the "World Wide Web" or simply the "Web". Examples of Browsers compatible with the present invention include the Internet Explorer program sold by Microsoft Corporation (Internet Explorer is a trademark of Microsoft Corporation), the Opera Browser program created by Opera Software ASA, or the Firefox browser program distributed by the Mozilla Foundation (Firefox is a registered trademark of the Mozilla Foundation). Although the following description details such operations in terms of a graphic user interface of a Browser, the present invention may be practiced with text based interfaces, or even with voice or visually activated interfaces, that have many of the functions of a graphic based Browser.

Browsers display information, which is formatted in a Standard Generalized Markup Language ("SGML") or a HyperText Markup Language ("HTML"), both being scripting languages, which embed non-visual codes in a text document through the use of special ASCII text codes. Files in these formats may be easily transmitted across computer networks, including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an eXtensible Markup Language ("XML") file, with XML files being capable of use with several Document Type Definitions ("DTD") and thus more general in nature than SGML or HTML. The XML file may be analogized to an object, as the data and the stylesheet formatting are separately contained (formatting may be thought of as methods of displaying information, thus an XML file has data and an associated method).

The terms "personal digital assistant" or "PDA", as defined above, means any handheld, mobile device that combines computing, telephone, fax, e-mail and networking features. The terms "wireless wide area network" or "WWAN" mean a wireless network that serves as the medium for the transmission of data between a handheld device and a computer. The term "synchronization" means the exchanging of information between a first device, e.g. a handheld device, and a second device, e.g. a desktop computer, either via wires or wirelessly. Synchronization ensures that the data on both devices are identical (at least at the time of synchronization).

In wireless wide area networks, communication primarily occurs through the transmission of radio signals over analog, digital cellular, or personal communications service ("PCS") networks. Signals may also be transmitted through microwaves and other electromagnetic waves. At the present time, most wireless data communication takes place across cellular systems using second generation technology such as code-division multiple access ("CDMA"), time division multiple access ("TDMA"), the Global System for Mobile Communications ("GSM"), Third Generation (wideband or "3G"), Fourth Generation (broadband or "4G"), personal digital cellular ("PDC"), or through packet-data technology over analog systems such as cellular digital packet data ("DPD") used on the Advance Mobile Phone Service ("AMPS").

The terms "wireless application protocol" or "WAP" mean a universal specification to facilitate the delivery and presentation of web-based data on handheld and mobile devices with small user interfaces. "Mobile Software" refers to the software operating system, which allows for application programs to be implemented on a mobile device such as a mobile telephone or PDA. Examples of Mobile Software are Java and Java ME (Java and JavaME are trademarks of Sun Microsystems, Inc. of Santa Clara, Calif.), BREW (BREW is a registered trademark of Qualcomm Incorporated of San Diego, Calif.), Windows Mobile (Windows is a registered trademark of Microsoft Corporation of Redmond, Wash.), Palm OS (Palm is a registered trademark of Palm, Inc. of Sunnyvale, Calif.), Symbian OS (Symbian is a registered trademark of Symbian Software Limited Corporation of London, United Kingdom), ANDROID OS (ANDROID is a registered trademark of Google, Inc. of Mountain View, Calif.), and iPhone OS (iPhone is a registered trademark of Apple, Inc. of Cupertino, Calif.), and Windows Phone 7. "Mobile Apps" refers to software programs written for execution with Mobile Software.

The terms "scan, fiducial reference", "fiducial location", "marker," "tracker" and "image information" have particular meanings in the present disclosure. For purposes of the present disclosure, "scan" or derivatives thereof refer to x-ray, magnetic resonance imaging (MRI), computerized tomography (CT), sonography, cone beam computerized tomography (CBCT), or any system that produces a quantitative spatial representation of a patient and a "scanner" is the means by which such scans are obtained. The term "fiducial key", or "fiducial reference", or simply "fiducial" refers to an object or reference on the image of a scan that is uniquely identifiable as a fixed recognizable point. In the present specification the term "fiducial location" refers to a useful location to which a fiducial reference is attached. A "fiducial location" will typically be proximate a surgical site. The term "marker" or "tracking marker" refers to an object or reference that may be perceived by a sensor proximate to the location of the surgical or dental procedure, where the sensor may be an optical sensor, a radio frequency identifier (RFID), a sonic motion detector, an ultra-violet or infrared sensor. The term "tracker" refers to a device or system of devices able to determine the location of the markers and their orientation and movement continually in 'real time' during a procedure. As an example of a possible implementation, if the markers are composed of printed targets then the tracker may include a stereo camera pair. In some embodiments, the tracker may be a non-stereo optical tracker, for example an optical camera. The camera may, for example, operate in the visible or near-infrared range. The term "image information" is used in the present specification to describe information obtained by the tracker, whether optical or otherwise, about one or more tracking markers and usable for determining the location of the markers and their orientation and movement continually in 'real time' during a procedure. In some embodiments, an imaging device may be employed to obtain real time close-up images of the surgical site quite apart from the tracker. In this specification, such imaging devices are described by the term "in situ imager" and the in situ imager may comprise an "illuminator" and an "imaging sensor". The term "vectorized" is used in this specification to describe fiducial keys, fiducial extensions, and tracking markers that are at least one of shaped or marked so as to make their orientation in three dimensions uniquely determinable from their appearance in a scan or in image information. If their three-dimensional orientation is determinable, then their three-dimensional location is also known.

FIG. 1 is a high-level block diagram of a computing environment 100 according to one embodiment. FIG. 1 illustrates server 110 and three clients 112 connected by network 114. Only three clients 112 are shown in FIG. 1 in order to simplify and clarify the description. Embodiments of the computing environment 100 may have thousands or millions of clients 112 connected to network 114, for example the Internet. Users (not shown) may operate software 116 on one of clients 112 to both send and receive messages network 114 via server 110 and its associated communications equipment and software (not shown).

Figure 2:
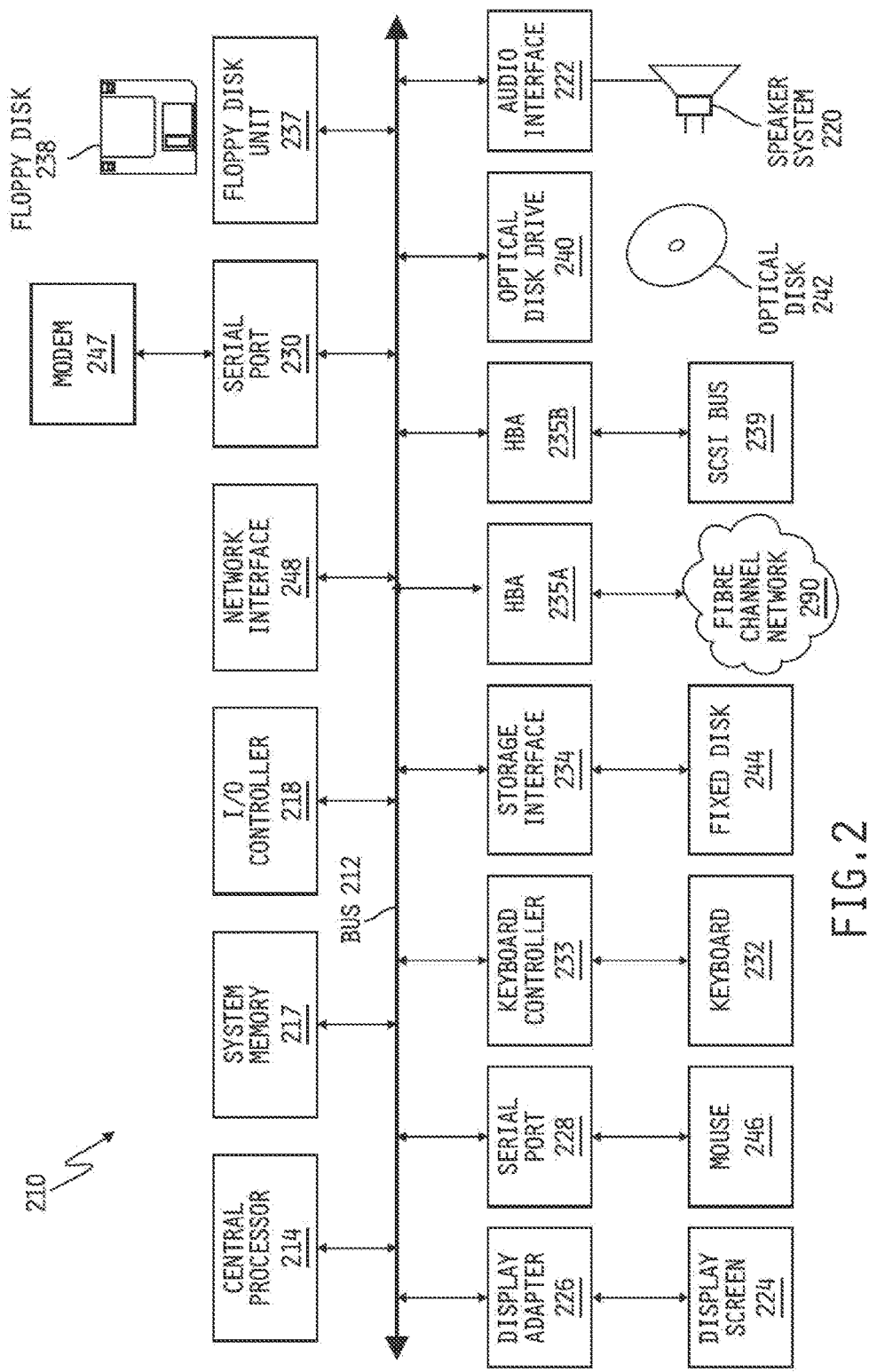
FIG. 2 is a block diagram of a computing system (either a server or client, or both, as appropriate), with optional input devices (e.g., keyboard, mouse, touch screen, etc.) and output devices, hardware, network connections, one or more processors, and memory/storage for data and modules, etc. which may be utilized as controller and display in conjunction with embodiments of the present invention.

FIG. 2 depicts a block diagram of computer system 210 suitable for implementing server 110 or client 112. Computer system 210 includes bus 212 which interconnects major subsystems of computer system 210, such as central processor 214, system memory 217 (typically RAM, but which may also include ROM, flash RAM, or the like), input/output controller 218, external audio device, such as speaker system 220 via audio output interface 222, external device, such as display screen 224 via display adapter 226, serial ports 228 and 230, keyboard 232 (interfaced with keyboard controller 233), storage interface 234, disk drive 237 operative to receive floppy disk 238, host bus adapter (HBA) interface card 235A operative to connect with Fiber Channel network 290, host bus adapter (HBA) interface card 235B operative to connect to SCSI bus 239, and optical disk drive 240 operative to receive optical disk 242. Also included are mouse 246 (or other point-and-click device, coupled to bus 212 via serial port 228), modem 247 (coupled to bus 212 via serial port 230), and network interface 248 (coupled directly to bus 212).

Bus 212 allows data communication between central processor 214 and system memory 217, which may include read-only memory (ROM) or flash memory (neither shown), and random access memory (RAM) (not shown), as previously noted. RAM is generally the main memory into which operating system and application programs are loaded. ROM or flash memory may contain, among other software code, Basic Input-Output system (BIOS), which controls basic hardware operation such as interaction with peripheral components. Applications resident with computer system 210 are generally stored on and accessed via computer readable media, such as hard disk drives (e.g., fixed disk 244), optical drives (e.g., optical drive 240), floppy disk unit 237, or other storage medium (memory stick, flash drive, etc.). Additionally, applications may be in the form of electronic signals modulated in accordance with the application and data communication technology when accessed via network modem 247 or interface 248 or other telecommunications equipment (not shown).

Storage interface 234, as with other storage interfaces of computer system 210, may connect to standard computer readable media for storage and/or retrieval of information, such as fixed disk drive 244. Fixed disk drive 244 may be part of computer system 210 or may be separate and accessed through other interface systems. Modem 247 may provide direct connection to remote servers via telephone link or the Internet via an Internet service provider (ISP) (not shown). Network interface 248 may provide direct connection to remote servers via direct network link to the Internet via a POP (point of presence). Network interface 248 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on), including the hardware components of FIGS. 3A-J, which alternatively may be in communication with associated computational resources through local, wide-area, or wireless networks or communications systems. Thus, while the disclosure may generally discuss an embodiment where the hardware components are directly connected to computing resources, one of ordinary skill in this area recognizes that such hardware may be remotely connected with computing resources. Conversely, all of the devices shown in FIG. 2 need not be present to practice the present disclosure. Devices and subsystems may be interconnected in different ways from that shown in FIG. 2. Operation of a computer system such as that shown in FIG. 2 is readily known in the art and is not discussed in detail in this application. Software source and/or object codes to implement the present disclosure may be stored in computer-readable storage media such as one or more of system memory 217, fixed disk 244, optical disk 242, or floppy disk 238. The operating system provided on computer system 210 may be a variety or version of either MS-DOS® (MS-DOS is a registered trademark of Microsoft Corporation of Redmond, Wash.), WINDOWS® (WINDOWS is a registered trademark of Microsoft Corporation of Redmond, Wash.), OS/2® (OS/2 is a registered trademark of International Business Machines Corporation of Armonk, N.Y.), UNIX® (UNLX is a registered trademark of X/Open Company Limited of Reading, United Kingdom), Linux® (Linux is a registered trademark of Linus Torvalds of Portland, Oreg.), or other known or developed operating system.

Moreover, regarding the signals described herein, those skilled in the art recognize that a signal may be directly transmitted from a first block to a second block, or a signal may be modified (e.g., amplified, attenuated, delayed, latched, buffered, inverted, filtered, or otherwise modified) between blocks. Although the signals of the above-described embodiments are characterized as transmitted from one block to the next, other embodiments of the present disclosure may include modified signals in place of such directly transmitted signals as long as the informational and/or functional aspect of the signal is transmitted between blocks. To some extent, a signal input at a second block may be conceptualized as a second signal derived from a first signal output from a first block due to physical limitations of the circuitry involved (e.g., there will inevitably be some attenuation and delay). Therefore, as used herein, a second signal derived from a first signal includes the first signal or any modification to the first signal, whether due to circuit limitations or due to passage through other circuit elements which do not change the informational and/or final functional aspect of the first signal.

The present invention relates to embodiments of surgical hardware and software monitoring systems and methods which allow for surgical planning while the patient is available for surgery, for example while the patient is being prepared for surgery so that the system may model the surgical site. The system uses a particularly configured piece of hardware, namely a fiducial reference, represented as fiducial key 10 in FIG. 3A, to orient tracking marker 12 of the monitoring system with regard to the critical area of the surgery. Single fiducial key 10 is attached to a location near the intended surgical area, in the exemplary embodiment of the dental surgical area of FIG. 3A, fiducial key 10 is attached to a dental splint 14. Tracking marker 12 may be connected to fiducial key 10 by tracking pole 11. In embodiments in which the fiducial reference is directly visible to a suitable tracker (see for example FIG. 5 and FIG. 6) that acquires image information about the surgical site, a tracking marker may be attached directly to the fiducial reference, being fiducial key 10 in the present embodiment. The tracker may be a non-stereo optical tracker. For example, in a dental surgical procedure, the dental tracking marker 14 may be used to securely locate the fiducial 10 near the surgical area. The single fiducial key 10 may be used as a point of reference, or a fiducial, for the further image processing of data acquired from tracking marker 12 by the tracker. In this arrangement, fiducial key or reference 10 is scanned not by the tracker, but by suitable scanning means, for example a non-stereo tracker. In other embodiments the tracker may be a stereo tracker. In some applications, the fiducial key 10 may be disposed in a location or in such orientation as to be at least in part non-visible to the tracker of the system.

In other embodiments additional tracking markers 12 may be attached to items independent of the fiducial key 10 and any of its associated tracking poles 11 or tracking markers 12. This allows the independent items to be tracked by the tracker.

In a further embodiment at least one of the items or instruments near the surgical site may optionally have a tracker attached to function as tracker for the monitoring system of the invention and to thereby sense the orientation and the position of the tracking marker 12 and of any other additional tracking markers relative to the scan data of the surgical area. By way of example, the tracker attached to an instrument may be a miniature digital camera and it may be attached, for example, to a dentist's drill. Any other markers to be tracked by the tracker attached to the item or instrument must be within the field of view of the tracker.

Using the dental surgery example, the patient is scanned to obtain an initial scan of the surgical site. The particular configuration of single fiducial key 10 allows computer software stored in memory and executed in a suitable controller, for example processor 214 and memory 217 of computer 210 of FIG. 2, to recognize its relative position within the surgical site from the scan data, so that further observations may be made with reference to both the location and orientation of fiducial key 10. In some embodiments, the fiducial reference includes a marking that is apparent as a recognizable identifying symbol when scanned. In other embodiments, the fiducial reference includes a shape that is distinct in the sense that the body apparent on the scan has an asymmetrical form allowing the front, rear, upper, and lower, and left/right defined surfaces that may be unambiguously determined from the analysis of the scan, thereby to allow the determination not only of the location of the fiducial reference, but also of its orientation. That is, the shape and/or markings of the fiducial reference render it vectorized. The marking and/or shape of fiducial key 10 allows it to be used as the single and only fiducial key employed in the surgical hardware and software monitoring system. By comparison, prior art systems typically rely on a plurality of fiducials. Hence, while the tracker may track several vectorized tracking markers within the monitoring system, only a single vectorized fiducial reference or key 10 of known shape or marking is required. By way of example, FIG. 5, later discussed in more detail, shows markers 506 and 502 tracked by tracker 508, but there is only one vectorized fiducial reference or key 502 in the system. FIG. 6 similarly shows three markers 604, 606, and 608 being tracked by tracker 610, while there is only a single vectorized fiducial reference or key 602 in the system.

In addition, the computer software may create a coordinate system for organizing objects in the scan, such as teeth, jaw bone, skin and gum tissue, other surgical instruments, etc. The coordinate system relates the images on the scan to the space around the fiducial and locates the instruments bearing markers both by orientation and position. The model generated by the monitoring system may then be used to check boundary conditions, and in conjunction with the tracker display the arrangement in real time on a suitable display, for example display 224 of FIG. 2.

In one embodiment, the computer system has a predetermined knowledge of the physical configuration of single fiducial key 10 and examines slices/sections of the scan to locate fiducial key 10. Locating of fiducial key 10 may be on the basis of its distinct shape, or on the basis of distinctive identifying and orienting markings upon the fiducial key or on attachments to the fiducial key 10 as tracking marker 12. Fiducial key 10 may be rendered distinctly visible in the scans through higher imaging contrast by the employ of radio-opaque materials or high-density materials in the construction of the fiducial key 10. In other embodiments the material of the distinctive identifying and orienting markings may be created using suitable high density or radio-opaque inks or materials.

Once fiducial key 10 is identified, the location and orientation of the fiducial key 10 is determined from the scan segments, and a point within fiducial key 10 is assigned as the center of the coordinate system. The point so chosen may be chosen arbitrarily, or the choice may be based on some useful criterion. A model is then derived in the form of a transformation matrix to relate the fiducial system, being fiducial key 10 in one particular embodiment, to the coordinate system of the surgical site. The resulting virtual construct may be used by surgical procedure planning software for virtual modeling of the contemplated procedure, and may alternatively be used by instrumentation software for the configuration of the instrument, for providing imaging assistance for surgical software, and/or for plotting trajectories for the conduct of the surgical procedure.

In some embodiments, the monitoring hardware includes a tracking attachment to the fiducial reference. In the embodiment pertaining to dental surgery the tracking attachment to fiducial key 10 is tracking marker 12, which is attached to fiducial key 10 via tracking pole 11. Tracking marker 12 may have a particular identifying pattern, described in more detail later at the hand of FIGS. 7-10. The trackable attachment, for example tracking marker 12, and even associated tracking pole 11 may have known configurations so that observational data from tracking pole 11 and/or tracking marker 12 may be precisely mapped to the coordinate system, and thus progress of the surgical procedure may be monitored and recorded. For example, as particularly shown in FIG. 3J, fiducial key 10 may have hole 15 in a predetermined location specially adapted for engagement with insert 17 of tracking pole 11. In such an arrangement, for example, tracking poles 11 may be attached with a low force push into hole 15 of fiducial key 10, and an audible haptic notification may thus be given upon successful completion of the attachment.

It is further possible to reorient the tracking pole during a surgical procedure. Such reorientation may be in order to change the location of the procedure, for example where a dental surgery deals with teeth on the opposite side of the mouth, where a surgeon switches hands, and/or where a second surgeon performs a portion of the procedure. For example, the movement of the tracking pole may trigger a re-registration of the tracking pole with relation to the coordinate system, so that the locations may be accordingly adjusted. Such a re-registration may be automatically initiated when, for example in the case of the dental surgery embodiment, tracking pole 11 With its attached tracking marker 12 are removed from hole 15 of fiducial key 10 and another tracking marker with its associated tracking pole is connected to an alternative hole on fiducial key 10. Additionally, boundary conditions may be implemented in the software so that the user is notified when observational data approaches and/or enters the boundary areas.

In a further embodiment, the tracking markers may specifically have a three dimensional shape. Suitable three-dimensional shapes bearing identifying patterns may include, without limitation, a segment of an ellipsoid surface and a segment of a cylindrical surface. In general, suitable three-dimensional shapes are shapes that are mathematically describable by simple functions.

The tracker of the system may comprise a single optical imager obtaining a two-dimensional image of the site being monitored. The system and method described in the present specification allow three-dimensional locations and orientations of vectorized tracking markers to be obtained using non-stereo-pair two-dimensional imagery. In some embodiments more than one imager may be employed as tracker, but the image information required and employed is nevertheless two-dimensional. Therefore the two imagers may merely be employed to secure different perspective views of the site, each imager rendering a two-dimensional image that is not part of a stereo pair. This does not exclude the employment of stereo-imagers in obtaining the image information about the site, but the system and method are not reliant on stereo imagery of the site.

In a further embodiment of the system utilizing the invention, a surgical instrument or implement, herein termed a "hand piece" (see FIGS. 5 and 6), may also have a particular configuration that may be located and tracked in the coordinate system and may have suitable tracking markers as described herein. A boundary condition may be set up to indicate a potential collision with virtual material, so that when the hand piece is sensed to approach the boundary condition an indication may appear on a screen, or an alarm sound. Further, target boundary conditions may be set up to indicate the desired surgical area, so that when the trajectory of the hand piece is trending outside the target area an indication may appear on screen or an alarm sound indicating that the hand piece is deviating from its desired path.

Figure 3A:
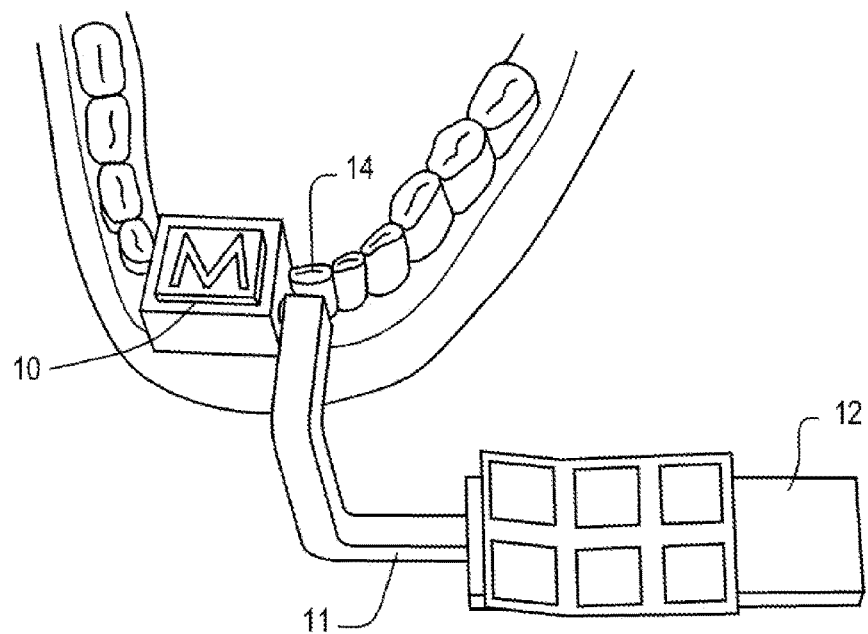
FIGS. 3A-J are drawings of hardware components of the surgical monitoring system according to embodiments of the invention.
Figure 3B:
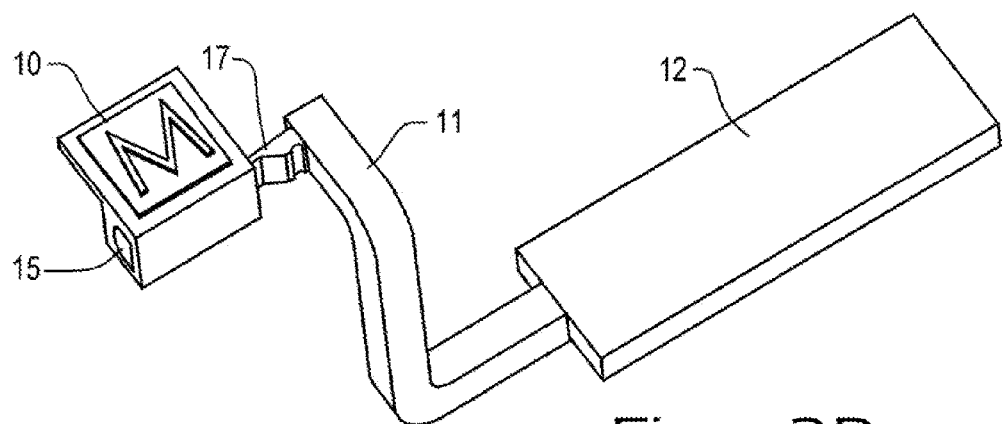
Figure 3C:
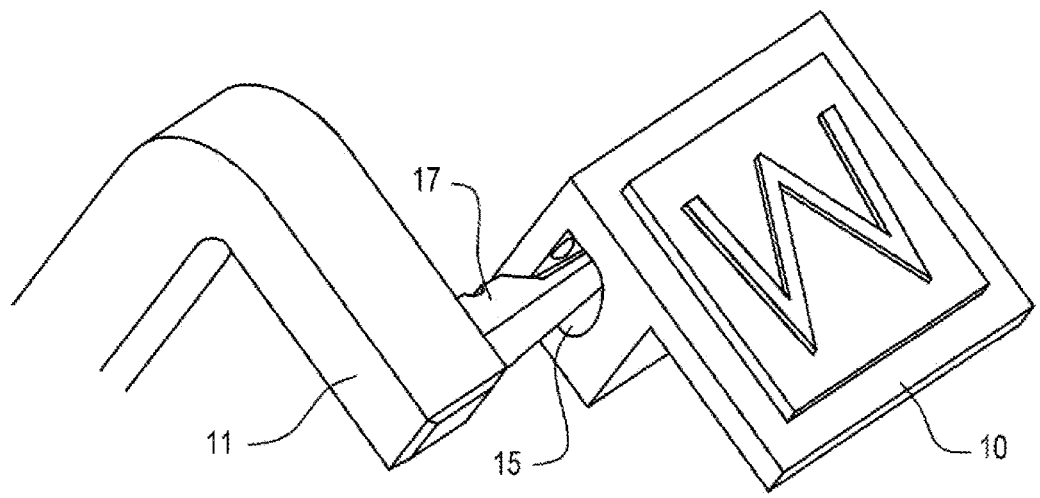
Figure 3D:
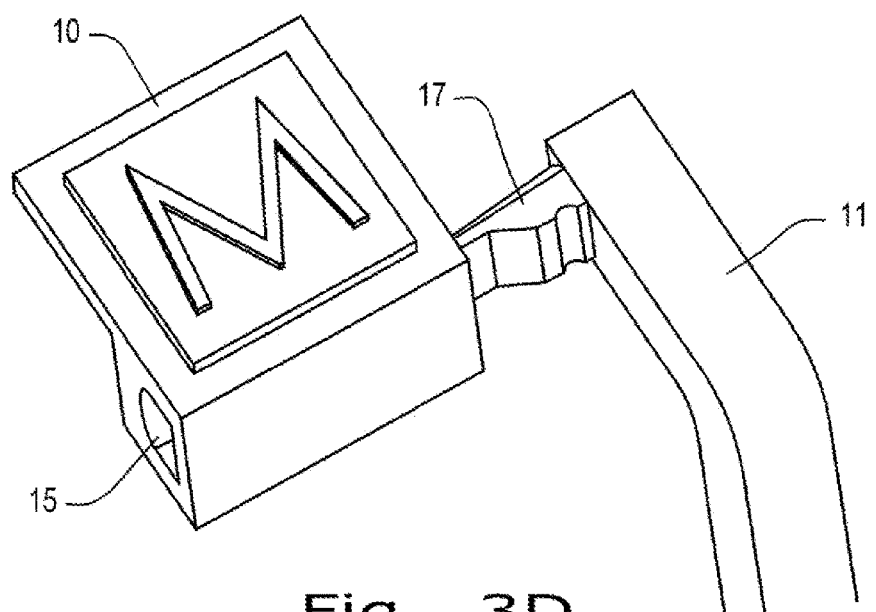
Figure 3E:
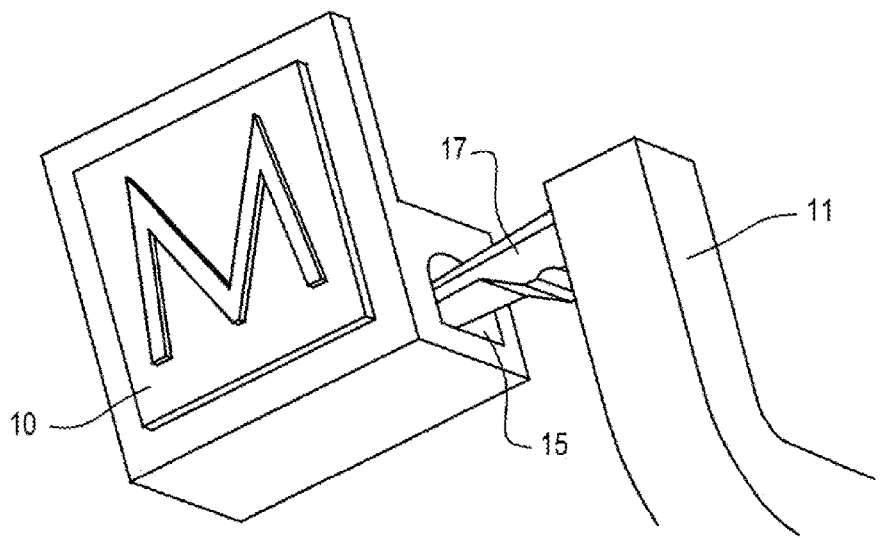
Figure 3F:
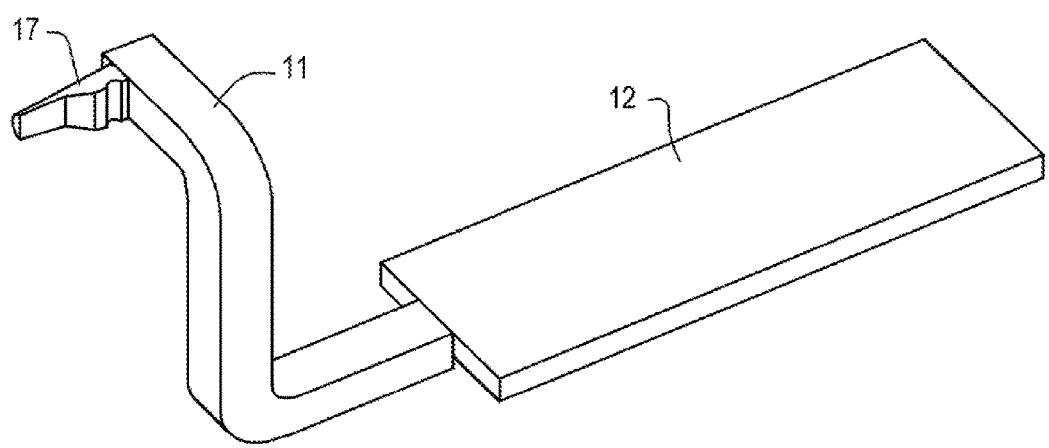
Figure 3G:
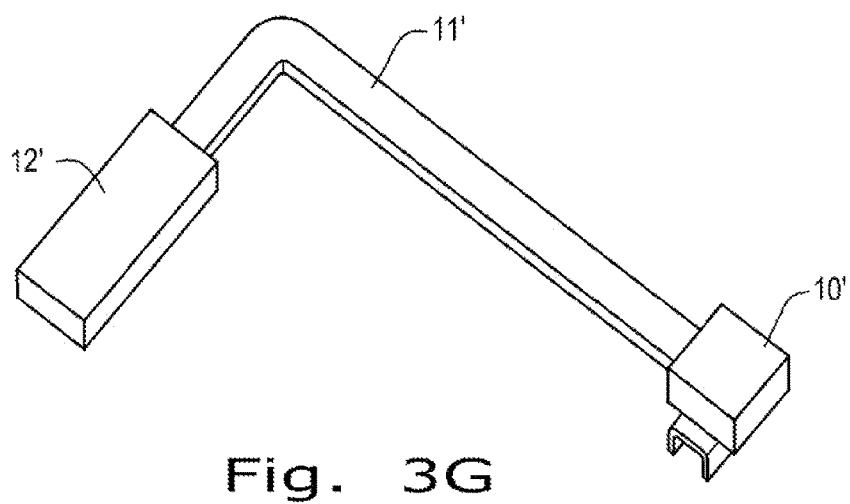
Figure 3H:
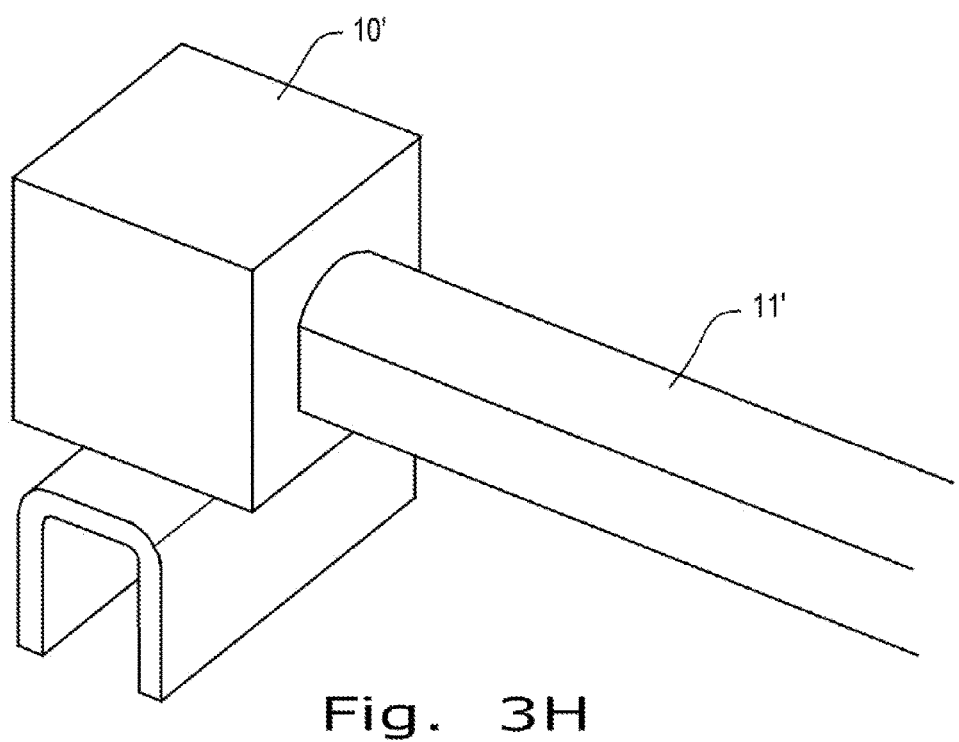
Figure 3I:
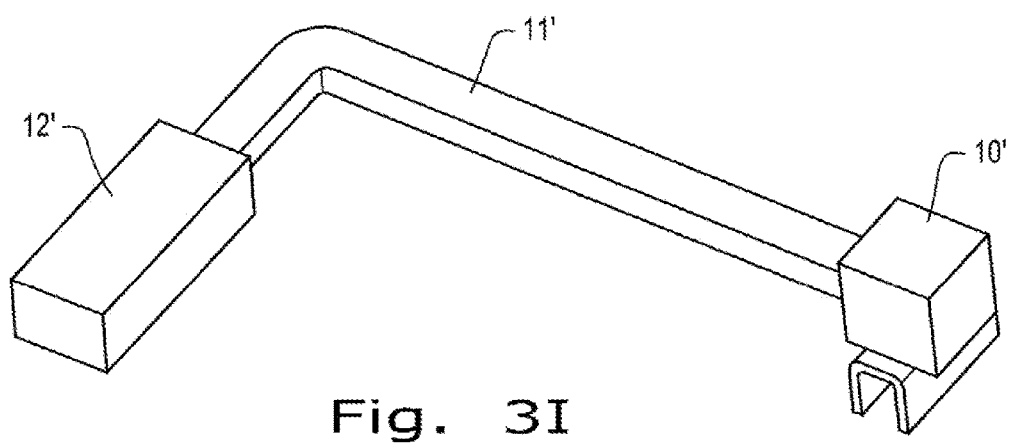
Figure 3J:
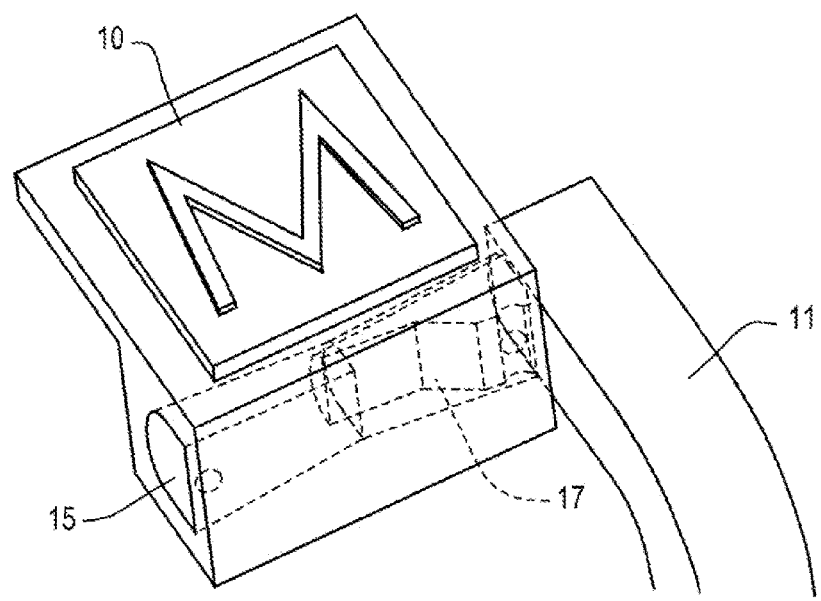

An alternative embodiment of some hardware components are shown in FIGS. 3G-I. Vectorized fiducial key 10' has connection elements with suitable connecting portions to allow a tracking pole 11' to position a tracking marker 12' relative to the surgical site. Conceptually, fiducial key 10' serves as an anchor for pole 11' and tracking marker 12' in much the same way as the earlier embodiment, although it has a distinct shape. The software of the monitoring system is pre-programmed with the configuration of each particularly identified fiducial key, tracking pole, and tracking marker, so that the location calculations are only changed according to the changed configuration parameters.

The materials of the hardware components may vary according to regulatory requirements and practical considerations. Generally, the key or fiducial component is made of generally radio opaque material such that it does not produce noise for the scan, yet creates recognizable contrast on the scanned image so that any identifying pattern associated with it may be recognized. In addition, because it is generally located on the patient, the material should be light-weight and suitable for connection to an apparatus on the patient. For example, in the dental surgery example, the materials of the fiducial key must be suitable for connection to a plastic splint and suitable for connection to a tracking pole. In the surgical example the materials of the fiducial key may be suitable for attachment to the skin or other particular tissue of a patient.

The tracking markers are clearly identified by employing, for example without limitation, high contrast pattern engraving. The materials of the tracking markers are chosen to be capable of resisting damage in autoclave processes and are compatible with rigid, repeatable, and quick connection to a connector structure. The tracking markers and associated tracking poles have the ability to be accommodated at different locations for different surgery locations, and, like the fiducial keys, they should also be relatively lightweight as they will often be resting on or against the patient. The tracking poles must similarly be compatible with autoclave processes and have connectors of a form shared among tracking poles.

The tracker employed in tracking the fiducial keys, tracking poles and tracking markers should be capable of tracking with suitable accuracy objects of a size of the order of 1.5 square centimeters. The tracker may be, by way of example without limitation, a stereo camera or stereo camera pair. While the tracker is generally connected by wire to a computing device to read the sensory input, it may optionally have wireless connectivity to transmit the sensory data to a computing device. In other embodiments, the tracker may be a non-stereo optical tracker. In other embodiments, the tracker may be a non-stereo optical tracker.

In embodiments that additionally employ a trackable piece of instrumentation, such as a hand piece, tracking markers attached to such a trackable piece of instrumentation may also be light-weight; capable of operating in a 3 object array with 90 degrees relationship; optionally having a high contrast pattern engraving and a rigid, quick mounting mechanism to a standard hand piece.

Figure 4A:
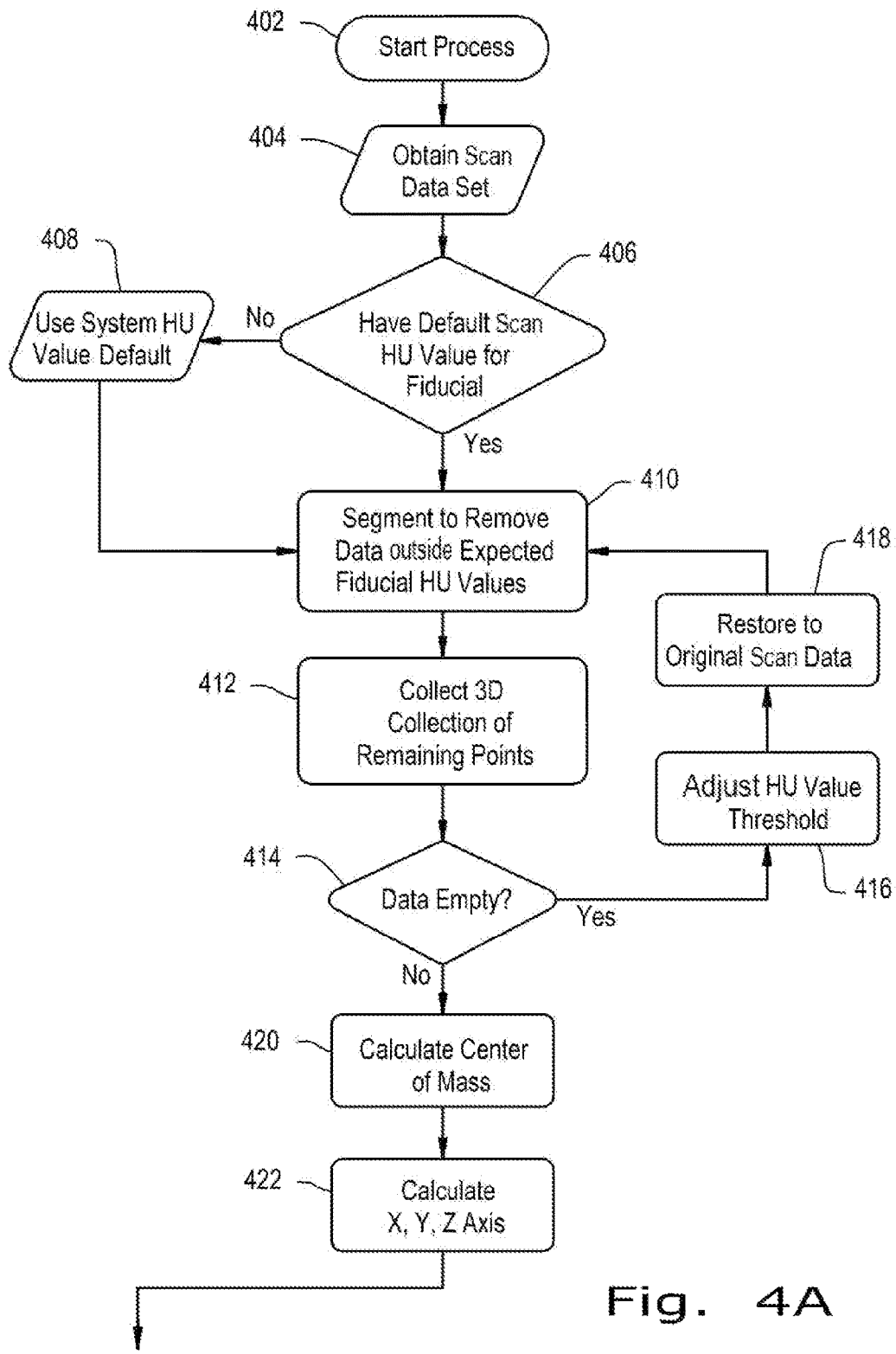
FIGS. 4A-C is a flow chart diagram illustrating one embodiment of the registering method of the present invention.
Figure 4B:
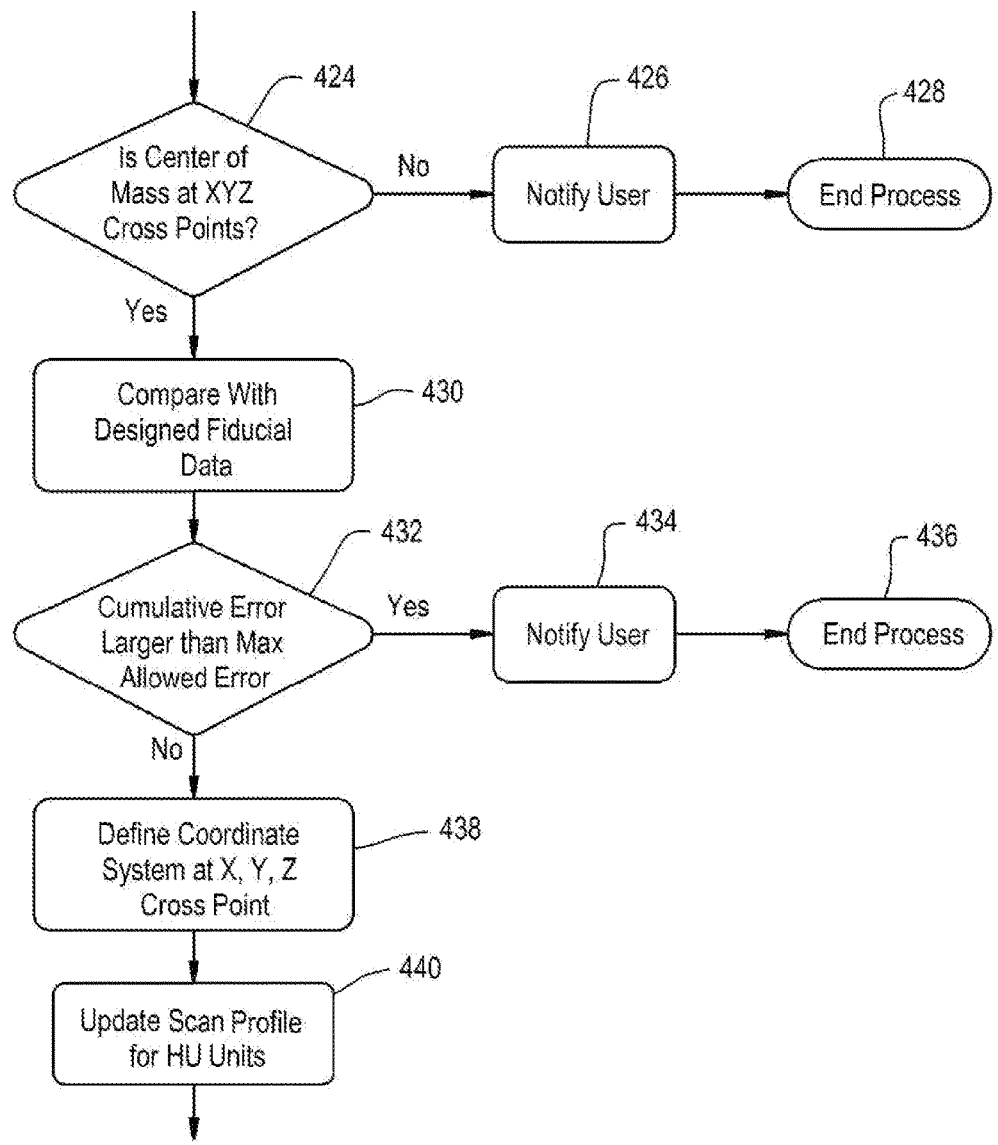
Figure 4C:
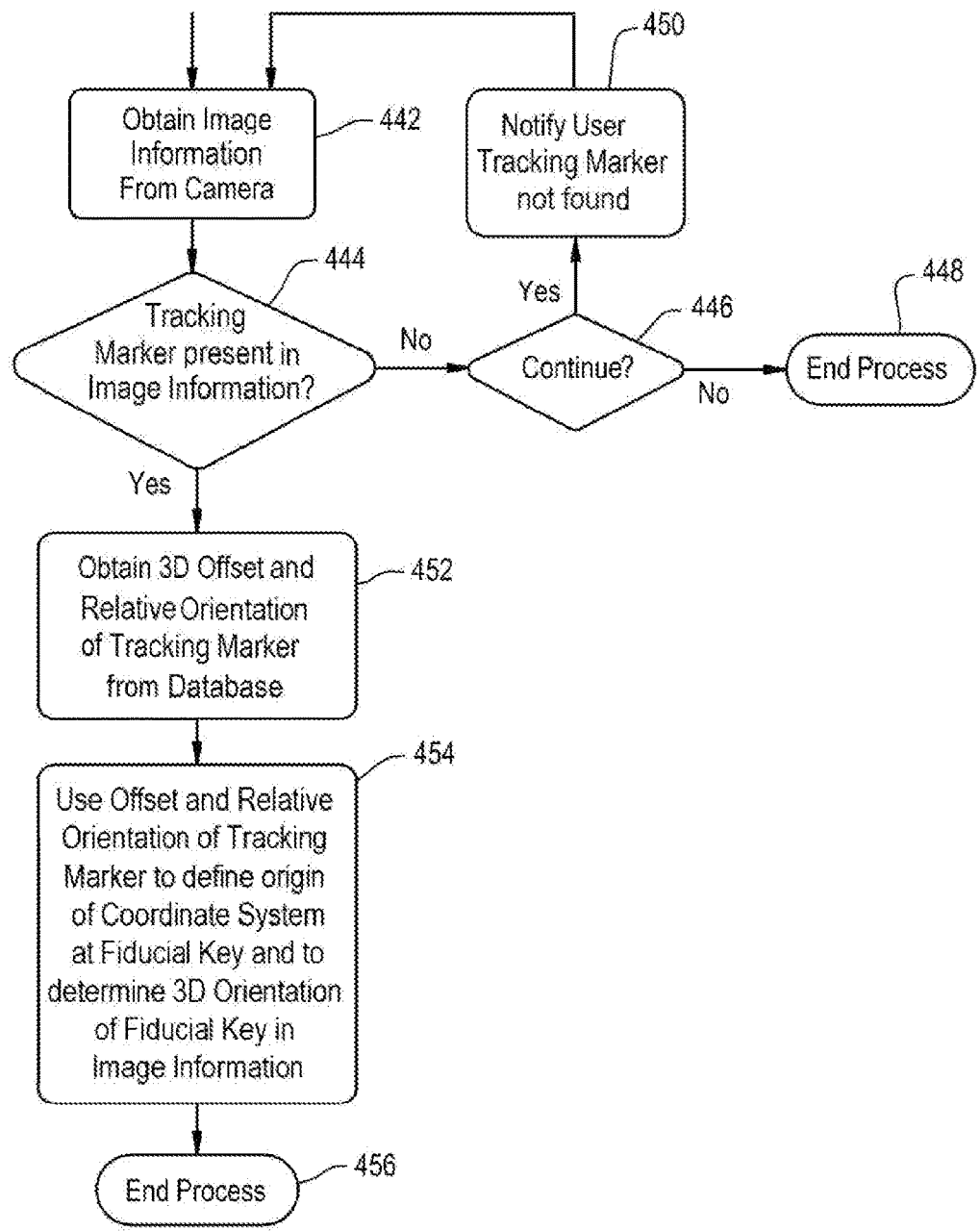

In another aspect there is presented an automatic registration method for tracking surgical activity, as illustrated in FIGS. 4A-C. FIG. 4A and FIG. 4B together present, without limitation, a flowchart of one method for determining the three-dimensional location and orientation of the fiducial reference from scan data. FIG. 4C presents a flow chart of a method for confirming the presence of a suitable tracking marker in image information obtained by the tracker and determining the three-dimensional location and orientation of the fiducial reference based on the image information.

Once the process starts [402], as described in FIGS. 4A and 4B, the system obtains a scan data set from, for example, a CT scanner and checks [at 406] for a default CT scan Hounsfield unit (HU) value for the vectorized fiducial which may or may not have been provided with the scan based on a knowledge of the fiducial and the particular scanner model, and if such a threshold value is not present, then a generalized predetermined default value is employed [408]. Next the data is processed by removing [at 410] scan segments with Hounsfield data values outside expected values associated with the fiducial key values, following the collection [at 412] of the remaining points. If the data is empty [at 414], the CT value threshold is adjusted [at 416], the original value restored [at 418], and the segmenting processing scan segments continues [at 410]. Otherwise, with the existing data a center of mass is calculated [at 420], along with calculating [at 422] the X, Y, and Z axes. If the center of mass is not at the cross point of the XYZ axes [at 424], then the user is notified [at 426] and the process stopped [at 428]. If the center of mass is at the XYZ cross point then the data points are compared [430] with the designed fiducial data. If the cumulative error is larger than the maximum allowed error [at 432] then the user is notified [at 434] and the process ends [at 436]. If not, then the coordinate system is defined [at 438] at the XYZ cross point, and the scan profile is updated for the HU units [at 440].

Turning now to FIG. 4C, image information is obtained [442] from the tracker, being a suitable camera or other sensor. The image information is two-dimensional and is not required to be a stereo image pair. The image information may be sourced from a single imaging device in the tracker, or may be sourced from multiple imaging devices in the tracker. It bears pointing out that the presence of multiple imaging devices in a tracker does not automatically imply stereo imaging. The image information is analyzed to determine whether a vectorized tracking marker is present in the image information [444]. If not, then the user is queried [446] as to whether the process should continue or not. If not, then the process is ended [448]. If the process is to continue, then the user can be notified [450] that no tracking marker has been found in the image information, and the process returns to obtaining image information [442]. If a tracking marker has been found based on the image information, or one has been attached by the user upon the above notification [at 450], the offset and relative orientation of the tracking marker to the fiducial reference is obtained from a suitable database. The term "database" is used in this specification to describe any source, amount or arrangement of such information, whether organized into a formal multi-element or multi-dimensional database or not. A single data set comprising offset value and relative orientation may suffice in a simple implementation of this embodiment of the invention and may be provided, for example, by the user or may be within a memory unit of the controller or in a separate database or memory.

The offset and relative orientation of the tracking marker is used to define the origin of a coordinate system at the fiducial reference and to determine [454] the three-dimensional orientation of the fiducial reference based on the image information and the registration process ends [456]. In order to monitor the location and orientation of the fiducial reference in real time, the process may be looped back from step [454] to obtain new image information from the camera [at 442]. A suitable query point may be included to allow the user to terminate the process. Detailed methods for determining orientations and locations of predetermined shapes or marked tracking markers from image data are known to practitioners of the art and will not be dwelt upon here. The coordinate system so derived is then used for tracking the motion of any items bearing tracking markers in the proximity of the surgical site. Other registration systems are also contemplated, for example using current other sensory data rather than the predetermined offset, or having a fiducial with a transmission capacity.

Figure 5:
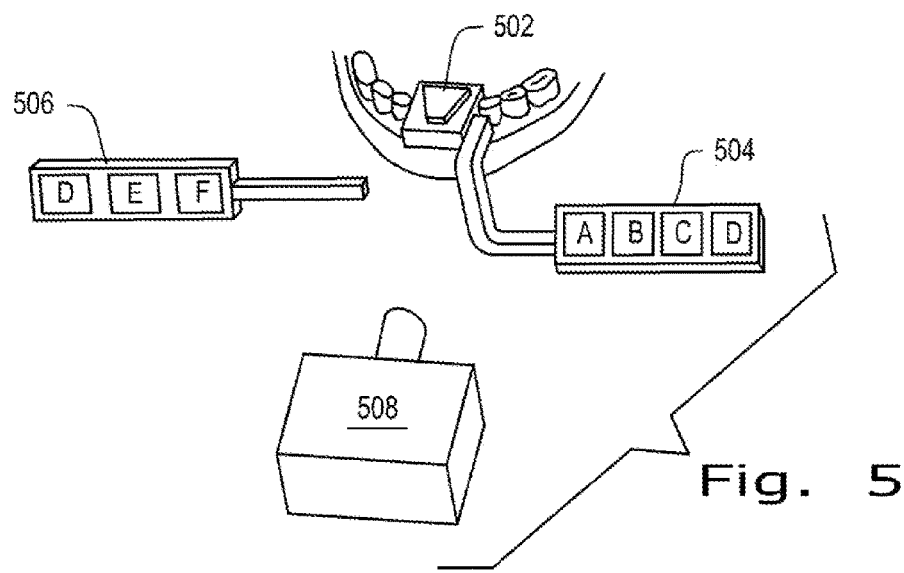
FIG. 5 is a drawing of a vectorized dental fiducial key with a tracking pole and a dental drill according to one embodiment of the present invention.
Figure 6:
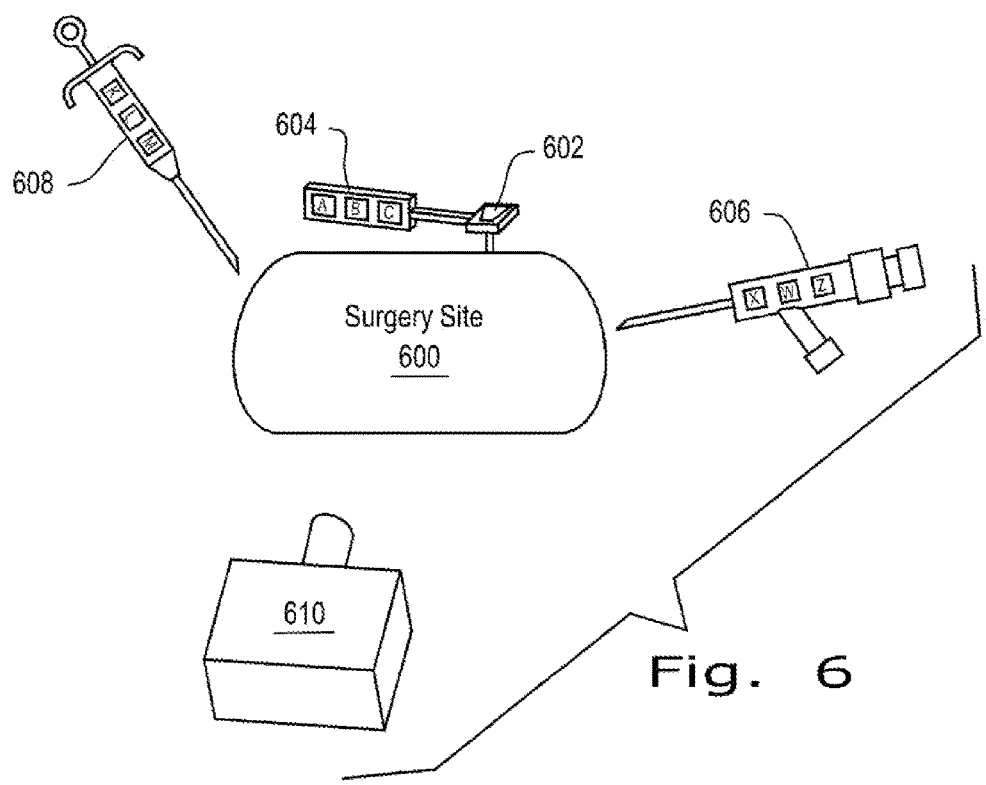
FIG. 6 is a drawing of an endoscopic surgical site showing the vectorized fiducial key, endoscope, and biopsy needle according to another embodiment of the invention.

One example of an embodiment of the invention is shown in FIG. 5. In addition to vectorized fiducial key 502 mounted at a predetermined tooth and having a rigidly mounted vectorized tracking marker 504, an additional instrument or implement 506, for example a hand piece which may be a dental drill, may be observed by a camera 508 serving as tracker of the monitoring system. The camera may be, for example, a non-stereo optical camera.

Another example of an embodiment of the invention is shown in FIG. 6. Surgery site 600, for example a human stomach or chest, may have vectorized fiducial key 602 fixed to a predetermined position to support tracking marker 604. Endoscope 606 may have further vectorized tracking markers, and biopsy needle 608 may also be present bearing a tracking marker at surgery site 600. Sensor 610 may be, for example, a camera, infrared sensing device, or RADAR. The camera may be, for example, a non-stereo optical camera.

Figure 8:
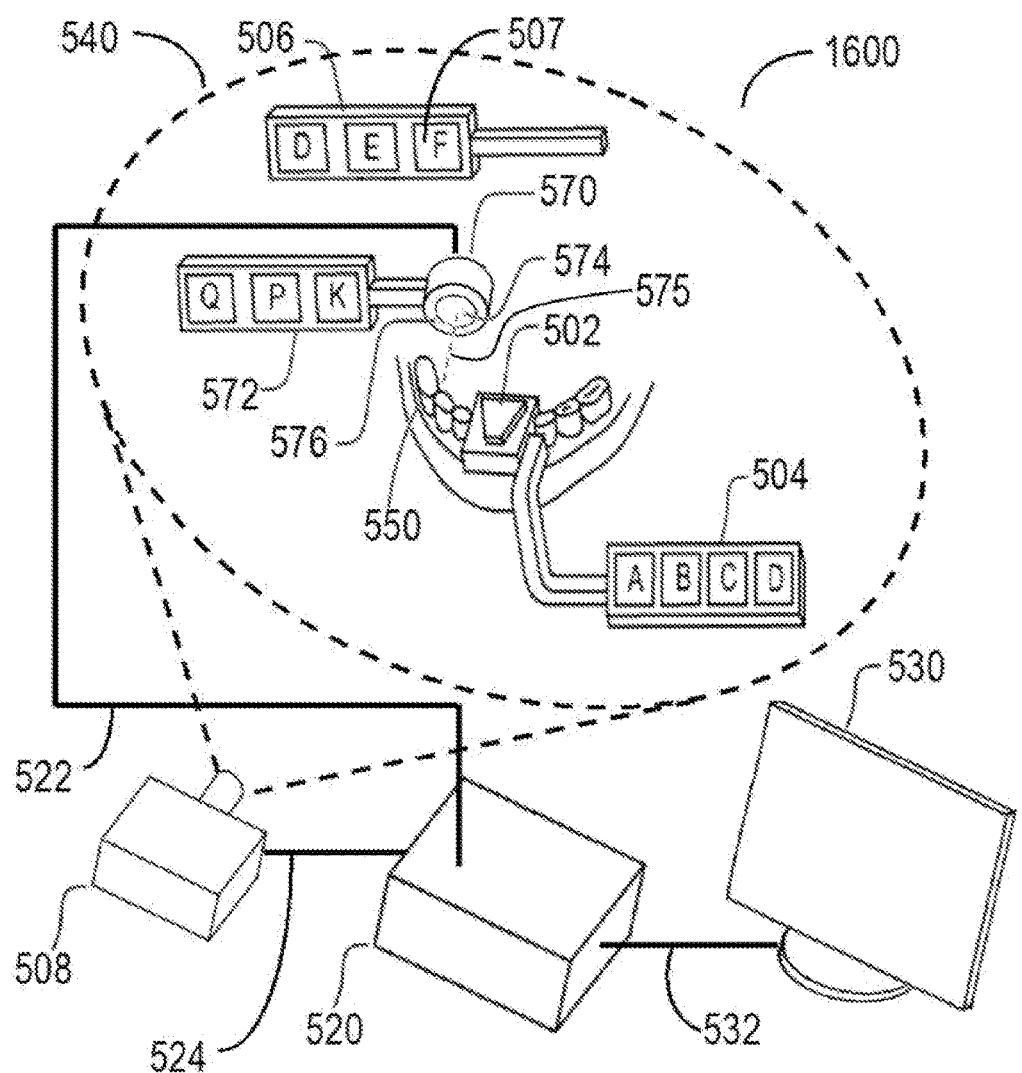
FIG. 8 is a drawing of a three-dimensional position and orientation tracking system according to yet another embodiment of the present invention.

In another aspect of the invention, most easily described at the hand of FIG. 8, there is provided a method for relating in real time the three-dimensional location and orientation of surgical site 550 on a patient to the location and orientation of the surgical site in a scan of surgical site 550, the method comprising removably attaching single vectorized fiducial reference 502 to a fiducial location on the patient proximate surgical site 550; performing the scan with single fiducial reference 502 attached to the fiducial location to obtain scan data; determining the three-dimensional location and orientation of the fiducial reference from the scan data; obtaining real time image information of surgical site 550 (using tracker 508); determining in real time the three-dimensional location and orientation of single fiducial reference 502 from the image information; deriving a spatial transformation matrix or expressing in real time the three-dimensional location and orientation of the fiducial reference as determined from the image information in terms of the three-dimensional location and orientation of single fiducial reference 502 as determined from the scan data.

Obtaining of real time image information from surgical site 550 may comprise rigidly and removably attaching to single fiducial reference 502 first vectorized tracking marker 504 in a fixed three-dimensional spatial relationship with single fiducial reference 502. First tracking marker 504 may be configured for having its location and its orientation determined based on the image information. Attaching first tracking marker 504 to single fiducial reference 502 may comprise rigidly and removably attaching first tracking marker 504 to the fiducial reference by means of a tracking pole. In this regard, see for example tracking pole 11 of FIG. 3B used to attach tracking marker 12 to fiducial reference 10. Obtaining the real time image information of the surgical site may comprise rigidly and removably attaching to the fiducial reference a tracking pole in a fixed three-dimensional spatial relationship with the fiducial reference, and the tracking pole may have a distinctly identifiable three-dimensional shape that allows its location and orientation to be uniquely determined from the image information.

In yet a further aspect of the invention, described at the hand of FIG. 8, there is provided a method for real time monitoring the position of an object, for example object 506, in relation to surgical site 550 of a patient, the method comprising removably attaching single vectorized fiducial reference 502 to a fiducial location on the patient proximate surgical site 550; performing a scan with single fiducial reference 502 attached to the fiducial location to obtain scan data; determining the three-dimensional location and orientation of single fiducial reference 502 from the scan data; obtaining real time image information of surgical site 550 (using tracker 508); determining in real time the three-dimensional location and orientation of single fiducial reference 502 from the image information; deriving a spatial transformation matrix for expressing in real time the three-dimensional location and orientation of single fiducial reference 502 as determined from the image information in terms of the three-dimensional location and orientation of single fiducial reference 502 as determined from the scan data; determining in real time the three-dimensional location and orientation of object 506 from the image information; and relating the three-dimensional location and orientation of object 506 to the three-dimensional location and orientation of the fiducial reference as determined from the image information. Determining in real time the three-dimensional location and orientation of the object from the image information may comprise rigidly attaching second vectorized tracking marker 507 to object 506.

Figure 7:
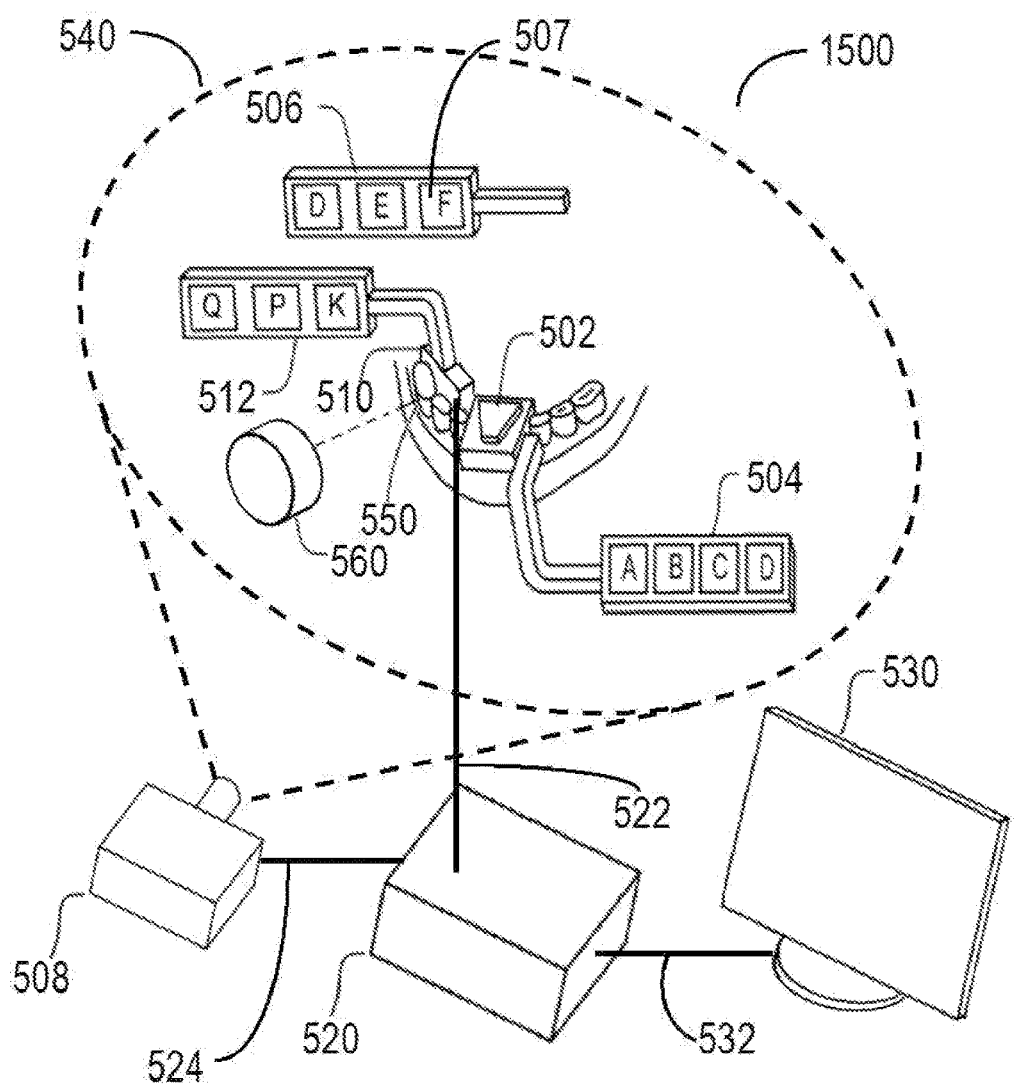
FIG. 7 is a drawing of a three-dimensional position and orientation tracking system according to another embodiment of the present invention.

A further embodiment is shown schematically (and not to scale) in FIG. 7, which is based on the elements already described at the hand of the dental surgery example of FIG. 5. Three-dimensional position and orientation tracking system 1500 comprises X-ray imaging sensor 510 bearing vectorized tracking marker 512. Tracking marker 512 is disposed within field of view 540 of tracker 508, with X-ray imaging sensor 510 disposed to obtain live X-ray images of surgical site 550 during a surgical procedure. These live X-ray images may be obtained on a continuous basis, or may consist of a continuous series of individual snapshots. Tracking marker 512 is rigidly attached either directly or indirectly to X-ray imaging sensor 510 in a predetermined fixed location on X-ray imaging sensor 510 and at a predetermined fixed orientation relative to the viewing axis of X-ray imaging sensor 510, given by a broken straight line in FIG. 15. X-ray imaging sensor 510 is served by a suitable X-ray source 560 illuminating the surgical site 550 with X-rays.

System tracker 508 obtains image information of the region within field of view 540 of system tracker 508. The image information is provided to system controller 520 by tracker 508 via tracker data link 524. In FIG. 7, tracker data link 524 is shown as a wired link, but in other embodiments tracker data link 524 may involve radio, optical, or other suitable wireless link. System controller 520 is programmable with software configuring it for extracting from the image information the 3D location and orientation information of vectorized tracking markers 504 and 512 by the methods already described in detail above at the hand of FIGS. 1 to 6.

The 3D location and orientation information of tracking marker 504 allows system controller 520 to directly compute the 3D location and orientation of fiducial reference 502. Since fiducial reference 502 is rigidly attached to surgical site 550 in a known relative 3D location and orientation relationship, system controller 520 may thereby compute the 3D location and orientation of surgical site 550.

The 3D location and orientation information of vectorized tracking marker 512 allows system controller 520 to directly compute the 3D location and orientation of X-ray imaging sensor 510. This allows system controller 520 to track in real time the 3D location and orientational view obtained by X-ray imaging sensor 510.

When surgical site 550 is illuminated with X-rays by X-ray source 560, system controller 520 may directly relate X-ray images of surgical site 550 received by system controller 520 via X-ray sensor data link 522 to the 3D location and orientation information of surgical site 550. Controller 520 may display the result on monitor 530 via monitor link 532. Data links 522 and 532 are shown as wired in FIG. 7, but in other embodiments data links 522 and 532 may involve radio, optical, or other suitable wireless link. Data links 522 and 532 ensure that the controller 520 is data-wise coupled to X-ray imaging sensor 510 and tracker 508 respectively.

The combination of the location and orientation information from tracking marker 504 and 3D-located and oriented live X-ray images from X-ray imaging sensor 510 allows the updating of information about surgical site 550 during the surgical procedure. This, in turn, allows a continuously updated 3D-based rendering of surgical site 550 on monitor or display system 530, via monitor data line 532, to assist in the surgical procedure. This allows monitor 530 to show during the surgical procedure the current live image of surgical site 550 in three-dimensional spatial relationship relative to the scan data. System 1500 determines from the scan data, the image information, and the live images a continuously updated 3-dimensional model of surgical site 550 overlaid with live imagery of surgical site 550.

As with the embodiment of FIG. 5, an additional instrument or implement 506, for example a hand piece that may be a dental drill, may be observed and tracked by tracker 508 of the monitoring system. To this end, implement 506 may bear third vectorized tracking marker 507. As already explained at the hand of FIG. 6, the same arrangement may also be applied to non-dental surgery.

In the embodiment described above at the hand of FIG. 7, illuminator 560 may also have a vectorized tracking marker (not shown in the interest of clarity) fixedly attached in a fixed three-dimensional location and orientation relative to illuminator 560. Given this known fixed 3D relationship, knowledge of the illumination cone of illuminator 560 allows the user to know where the illumination will be impinging once the location and orientation of the tracking marker on illuminator 560 is known. With illuminator 560 disposed in field of view 540 of tracker 508, system controller 520 may extract from the image information provided by tracker 508 the three-dimensional location and orientation of the tracking marker attached to illuminator 560 and display on monitor 530 an indication of where illuminator 560 will illuminate the patient at any given time. This allows the user to adjust the positioning of illuminator 560 proximate surgical site 550.

Another embodiment is described at the hand of FIG. 8. Every element of FIG. 8 bearing the same number as in FIG. 7 is to be understood as being the same element and performing the same function as in FIG. 7. In the embodiment of monitoring system 1600 shown in FIG. 8, in situ imager 570 comprises imaging sensor 574 for imaging surgical site 550 and illuminator 576 for illuminating surgical site 550 with radiation. Illuminator 576 may employ visible light radiation allowing imaging sensor 574 to image surgical site 550. In some implementations, illuminator 576 may employ exciting radiation, for example without limitation blue light, ultra-violet light, or other exciting radiation for exciting tissue to selectively fluoresce and emit light of a longer or shorter wavelength. Imaging sensor 574 may be an imaging sensor sensitive to the illuminating radiation from illuminator 576. In some implementations, illuminator 576 may be an annular illuminator disposed around imaging sensor 574. In other implementations, illuminator 576 and imaging sensor 574 may be separate devices, with imaging sensor 574 directly or indirectly bearing the rigidly attached tracking sensor 572.

When exciting radiation from illuminator 576 is employed to induce fluorescence in the tissue of surgical site 550, imaging sensor may be sensitive to the induced fluorescence light wavelengths and may be rendered specifically insensitive to the exciting radiation wavelength by means of suitable optical filters. In yet other implementations, in situ imager 570 may be equipped with both visible imaging facilities and fluorescence imaging facilities in order to superimpose the fluorescence image on the visible image. In yet other implementations the illuminating radiation may be of one spectrum of wavelengths while the imaging sensor 574 employs a different spectrum chosen to improve imaging contrast within imaging sensor 574.

Tracking marker 572 is attached directly or indirectly to imaging sensor 574 in a predetermined fixed location with respect to imaging sensor 574 and at a predetermined fixed orientation relative to the viewing axis of imaging sensor 574, given by broken straight line 575 in FIG. 8. System controller 520 receives live images of the surgical site over sensor data link 526 which ensures that controller 520 is data-wise coupled to imaging sensor 574. The embodiment of FIG. 8 therefore differs from the embodiment of FIG. 7 in that the means of imaging is reflective or fluoroscopic, while the means of imaging in FIG. 7 is X-ray transmissive. In both embodiments illuminator 560, 576 is employed and in both embodiments a live image, being either continuously generated images or comprising intermittent snapshots, is obtained of the surgical site 550 by an imaging sensor 510, 574. In both cases the live image of surgical site 550 is communicated to system controller 520 via sensor data link 522, 526. The live images may be one or more of reflected visible light images, fluoroscopic images employing fluorescent light emitted from fluorescing tissue, and X-ray transmission images. The corresponding live images may be obtained from imaging sensor 510, 574 when surgical site 550 is illuminated with suitable radiation from a visible light source; short wavelength visible or ultra-violet light source; and an X-ray source as illuminator respectively. Suitable short wavelength visible light may be, for example, one or more of blue light and violet light.

In FIG. 8, illuminator 576 and imaging sensor 574 are shown as housed together for the sake of convenience within in situ imager 570. In other embodiments, illuminator 576 and imaging sensor 574 may be housed separately and may be separately tagged with vectorized tracking markers of the same type as vectorized tracking markers 504, 507 and 572, and may be separately tracked by tracker 508. With illuminator 576 disposed in field of view 540 of tracker 508, system controller 520 may extract from the image information provided by tracker 508 the three-dimensional location and orientation of the tracking marker attached to illuminator 576 and display on monitor 530 an indication of where illuminator 576 will illuminate the patient at any given time. This allows the user to adjust the positioning of illuminator 576 proximate surgical site 550.

As with the embodiment of FIG. 5 and as described at the hand of FIG. 7, an additional instrument or implement 506, for example a hand piece that may be a dental drill, may be observed and tracked by tracker 508 of the monitoring system. To this end, implement 506 may bear third vectorized tracking marker 507. As already explained at the hand of FIG. 6, the same arrangement may also be applied to non-dental surgery.

Figure 9:
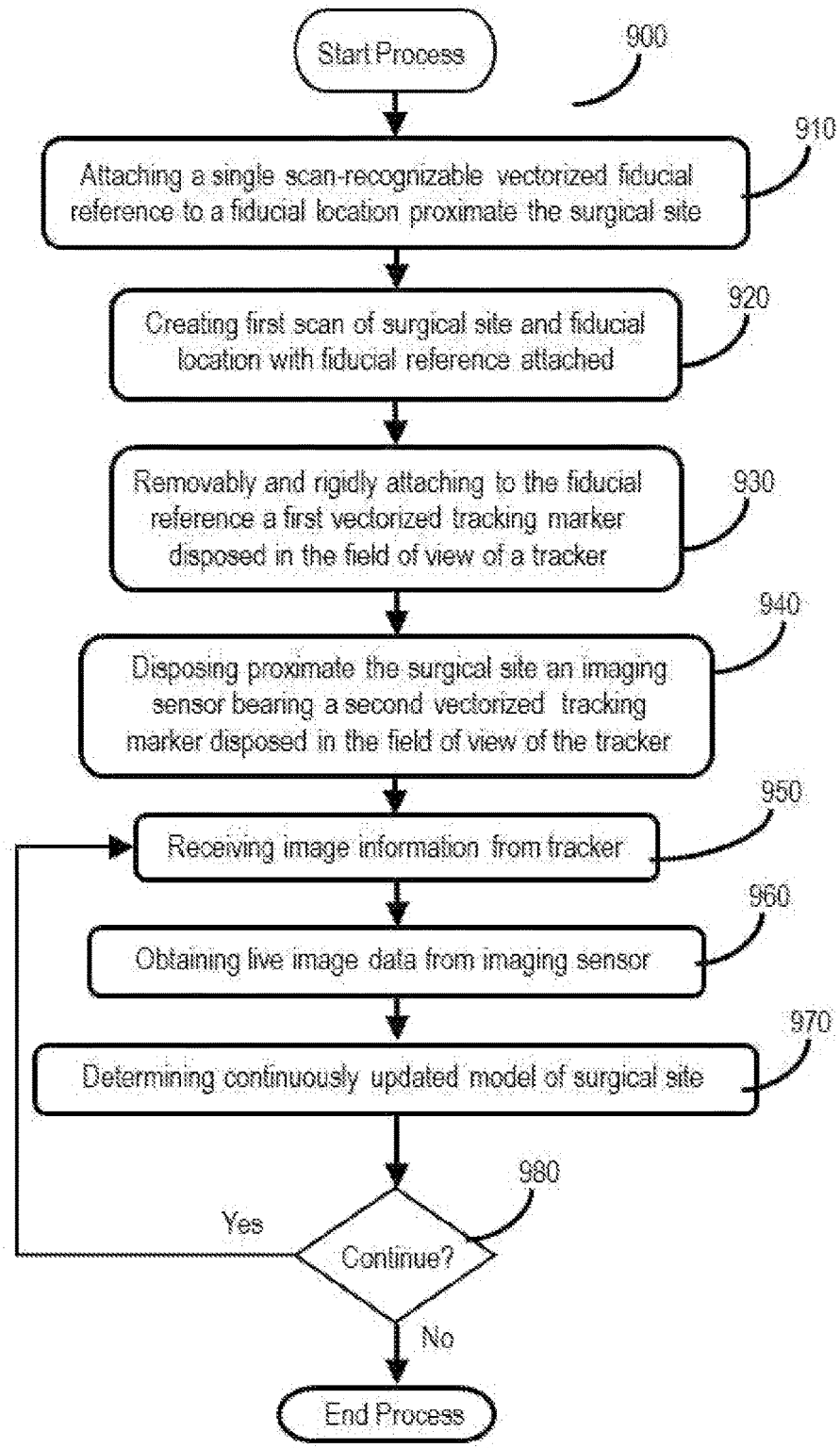
FIG. 9 is a flow chart illustrating a method for monitoring a surgical site.

In another aspect, described at the hand of the flow chart of FIG. 9, a method [900] is provided for monitoring a surgical site 550, the method [900] comprising: removably attaching [910] vectorized fiducial reference 502 to a fiducial location proximate surgical site 550, the fiducial reference having a at least one of a marking and a shape perceptible on a scan; creating [920] prior to the surgical procedure a scan of surgical site 550 and the fiducial location with fiducial reference 502 attached; removably and rigidly attaching [930] to the fiducial reference 502 first vectorized tracking marker 504 disposed in field of view 540 of tracker 508; disposing [940] proximate surgical site 550 imaging sensor 510, 574 bearing second vectorized tracking marker 512, 572 disposed in the field of view of tracker 508; receiving [950] from tracker 508 image information of at least surgical site 550 and tracking markers 504, 512, 572; obtaining [960] from imaging sensor 510, 574 live images of surgical site 550; and determining [970] from the scan data, the image information, and the live images a continuously updated 3-dimensional model of surgical site 550 overlaid with live imagery of surgical site 550 as obtained by the imaging sensor.

After every image from imaging sensor 510, 574 has been overlaid on the scan data, the process may selectably return [980] to step [950] to receive new image information from tracker 508 and a corresponding new live image from imaging sensor 510, 574. The obtaining [960] live images may comprise illuminating the surgical site with at least one of X-ray radiation, exciting radiation, and reflective optical radiation by means of the illuminator 560, 576. The different kinds of imaging sensors 510, 574 and their modes of working have already been described above, as have illuminators 560, 576. Determining the continuously updated three-dimensional model of surgical site 550 comprises determining from the first scan data a three-dimensional location and orientation of vectorized fiducial reference 502 relative to the surgical site; and determining from the image information three-dimensional location and orientation information about first 504 and second 512, 572 vectorized tracking markers. In some embodiments, the determining the continuously updated three-dimensional model of surgical site 550 may further comprise determining from the image information three-dimensional location and orientation information about third vectorized tracking marker 507.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A position monitoring system for a surgical procedure comprising:
   a single vectorized fiducial reference adapted to be fixed to a surgical site of a surgical patient;
   an imaging sensor adapted to be disposed proximate the surgical site and adapted to provide live image data of the surgical site;
   an illuminator adapted for illuminating the surgical site with radiation;
   a first vectorized tracking marker rigidly attached in a predetermined fixed three-dimensional position and orientation relative to the single fiducial reference;
   a second vectorized tracking marker rigidly attached in a predetermined fixed three-dimensional position and orientation relative to the imaging sensor;
   a tracker configured and disposed for obtaining image information of at least the first and second tracking markers;
   a controller coupled to the tracker and to the imaging sensor and comprising a processor with memory, the memory storing scan data and a software program, the scan data representative of the surgical site before the surgical procedure with the single fiducial reference fixed to the surgical site and the software program having a series of instructions which when executed by the processor determines from the image information current positions and orientations of the first and second tracking markers, and relates the scan data to the current three-dimensional position and orientation of the single fiducial reference and to the current live image data of the surgical site; and
   a display system coupled to the controller and adapted to show during the surgical procedure the current live image of the surgical site in three-dimensional spatial relationship relative to the scan data.

2. The system of claim 1, further comprising a surgical implement bearing a third vectorized tracking marker, wherein:
   the tracker is further configured and disposed for obtaining image information of the third tracking marker; and
   the software program has a further series of instructions which when executed by the processor determines from the image information the current position and orientation of the third tracking marker and relates the scan data to the current position and orientation of the surgical implement.

3. The system of claim 1, wherein the tracker is an optical tracker.

4. The system of claim 3, wherein the optical tracker is a non-stereo optical tracker.

5. The system of claim 3, wherein the optical tracker is a stereo optical tracker.

6. The system of claim 1, wherein the single fiducial reference is at least partially non-visible when fixed to the surgical site.

7. A method for monitoring a surgical site, comprising the steps of:
   removably attaching a single vectorized fiducial reference to a fiducial location proximate a surgical site, the fiducial reference being perceptible on a scan;

creating prior to the surgical procedure a scan of the surgical site and the fiducial location with the single fiducial reference attached;

removably and rigidly attaching to the single fiducial reference a first vectorized tracking marker disposed within a field of view of a tracker;

disposing proximate the surgical site an imaging sensor bearing a second vectorized tracking marker disposed in the field of view of tracker;

receiving from the tracker image information of at least the surgical site and the first and second tracking markers;

obtaining from the imaging sensor live images of the surgical site;

determining from the scan data, the image information, and the live images of the surgical site a continuously updated 3-dimensional model of the surgical site overlaid with live imagery of the surgical site.

8. The method of claim 7, wherein the step of determining the continuously updated three-dimensional model of the surgical site comprises:

determining from the scan data a three-dimensional location and orientation of the single fiducial reference relative to the surgical site based on at least one of markings on and the shape of the single fiducial reference;

determining from the image information three-dimensional location and orientation information about the first and second tracking markers; and calculating from the three-dimensional locations and orientations of the first and second tracking markers the corresponding three-dimensional locations and orientations of the single fiducial reference and imaging sensor respectively.

9. The method of claim 7, wherein the step of determining the continuously updated three-dimensional model of the surgical site further comprises:

determining from the image information three-dimensional location and orientation information about a third vectorized tracking marker fixedly attached to a surgical implement; and calculating from the three-dimensional location and orientation of the third tracking marker the corresponding three-dimensional location and orientation of the surgical implement.

10. The method of claim 7, wherein the step of receiving image information comprises receiving optical image information.

11. The method of claim 10, wherein the step of receiving optical image information comprises receiving non-stereo optical image information.

12. The method of claim 7, wherein the step of removably attaching the single fiducial reference comprises removably attaching the single fiducial reference to be disposed at least partly non-visible to the tracker.

13. The method of claim 7, wherein the step of obtaining live images comprises obtaining live optical images.

14. The method of claim 13, wherein the step of obtaining live optical images comprises obtaining live fluoroscopic images.

15. The method of claim 13, wherein the step of obtaining live optical images comprises obtaining live optical images based on reflected light.

16. The method of claim 7, wherein the step of obtaining live images comprises obtaining live X-ray transmission images.

17. The method of claim 7, wherein the step of obtaining live images comprises illuminating the surgical site with radiation.

18. The method of claim 17, wherein the radiation is X-ray radiation.

19. The method of claim 17, wherein the radiation is exciting radiation.

20. The method of claim 17, wherein the radiation is reflective optical radiation.

* * * * *